United States Patent
Metha et al.

(10) Patent No.: US 10,647,621 B2
(45) Date of Patent: May 12, 2020

(54) PHOTOCATALYTIC CONVERSION OF CARBON DIOXIDE AND WATER INTO SUBSTITUTED OR UNSUBSTITUTED HYDROCARBON(S)

(71) Applicants: Adelaide Research and Innovation, Adelaide (AU); Flinders University of South Australia, Bedford Park (AU); University of Canterbury, Christchurch (NZ); University of South Australia, Adelaide (AU)

(72) Inventors: Gregory F Metha, Adelaide (AU); Gunther Andersson, Bedford Park (AU); Vladimir Golovko, Christchurch (NZ); Thomas Nann, Adelaide (AU)

(73) Assignees: Adelaide Research and Innovation, The University of Adelaide, Adelaide South Australia (AU); Flinders University of South Australia, South Australia (AU); University of Canterbury, Christchurch (NZ); University of South Australia, Adelaide South Australia (AU)

(*) Notice: Subject to any disclaimer, the term of this patent is extended or adjusted under 35 U.S.C. 154(b) by 0 days.

(21) Appl. No.: 15/780,078

(22) PCT Filed: Nov. 30, 2016

(86) PCT No.: PCT/AU2016/051175
§ 371 (c)(1),
(2) Date: May 30, 2018

(87) PCT Pub. No.: WO2017/091857
PCT Pub. Date: Jun. 8, 2017

(65) Prior Publication Data
US 2019/0002364 A1    Jan. 3, 2019

(30) Foreign Application Priority Data

Nov. 30, 2015   (AU) ................................ 2015904952

(51) Int. Cl.
    *C07C 1/12*    (2006.01)
    *B01J 23/52*   (2006.01)
    (Continued)

(52) U.S. Cl.
    CPC ............... *C07C 1/12* (2013.01); *B01J 21/063* (2013.01); *B01J 21/18* (2013.01); *B01J 23/42* (2013.01);
    (Continued)

(58) Field of Classification Search
    CPC ........... C07C 1/12; C07C 9/04; C07C 29/157; C07C 31/04; C07C 2523/42;
    (Continued)

(56) References Cited

U.S. PATENT DOCUMENTS

| 4,847,231 A | 7/1989 | Gratzel et al. |
| 6,121,191 A | 9/2000 | Komatsu |

(Continued)

FOREIGN PATENT DOCUMENTS

| WO | 2014181355 | 11/2014 |
| WO | 2015109217 | 7/2015 |

OTHER PUBLICATIONS

Uzunova et al., CO2 conversion to methanol on Cu(I) oxide nanolayers and clusters Physical Chemistry Chemical Physics (2015), 17(16), 11088-11094.*
(Continued)

*Primary Examiner* — Jafar F Parsa
(74) *Attorney, Agent, or Firm* — Cooper & Dunham LLP

(57) ABSTRACT

A method for the production of hydrocarbon(s), such as methane, substituted hydrocarbons, such as methanol, or the
(Continued)

production of hydrogen, the method comprising the steps of contacting a first catalyst with water in order to photocatalyse the splitting of at least some of the water into hydrogen and oxygen; and contacting a second catalyst with a gas stream comprising carbon dioxide and at least some of the hydrogen produced from step (a) in order to photocatalyse the reaction between the hydrogen and carbon dioxide to produce hydrocarbon(s), such as methane, and/or substituted hydrocarbons, such as methanol. In an embodiment, the catalyst comprises gold and or ruthenium nanoclusters supported on a substrate.

15 Claims, 23 Drawing Sheets

(51) Int. Cl.
| | |
|---|---|
| C07C 29/157 | (2006.01) |
| B01J 21/06 | (2006.01) |
| B01J 21/18 | (2006.01) |
| B01J 23/46 | (2006.01) |
| B01J 35/00 | (2006.01) |
| B01J 31/22 | (2006.01) |
| B01J 23/42 | (2006.01) |
| B01J 31/24 | (2006.01) |
| C10G 2/00 | (2006.01) |
| C01B 3/04 | (2006.01) |
| B01J 37/16 | (2006.01) |
| C01B 3/06 | (2006.01) |
| C07C 9/04 | (2006.01) |
| C07C 31/04 | (2006.01) |
| B01J 37/03 | (2006.01) |

(52) U.S. Cl.
CPC ............ *B01J 23/462* (2013.01); *B01J 23/52* (2013.01); *B01J 31/226* (2013.01); *B01J 31/2208* (2013.01); *B01J 31/2404* (2013.01); *B01J 31/2409* (2013.01); *B01J 35/004* (2013.01); *B01J 35/006* (2013.01); *B01J 35/0013* (2013.01); *B01J 37/16* (2013.01); *C01B 3/042* (2013.01); *C01B 3/061* (2013.01); *C07C 9/04* (2013.01); *C07C 29/157* (2013.01); *C07C 31/04* (2013.01); *C10G 2/333* (2013.01); *B01J 37/031* (2013.01); *B01J 2231/625* (2013.01); *B01J 2531/0211* (2013.01); *B01J 2531/0222* (2013.01); *B01J 2531/18* (2013.01); *C07C 2521/06* (2013.01); *C07C 2523/42* (2013.01); *C07C 2523/46* (2013.01); *C07C 2523/52* (2013.01); *Y02P 20/52* (2015.11)

(58) Field of Classification Search
CPC ....... C07C 2523/52; B01J 23/52; B01J 37/16; B01J 35/0013; B01J 21/63; B01J 21/18; B01J 23/42; B01J 23/462; B01J 35/004; C01B 3/061; C01B 3/042; C10G 2/333
See application file for complete search history.

(56) References Cited

U.S. PATENT DOCUMENTS

| | | |
|---|---|---|
| 2005/0159306 A1 | 7/2005 | Kezuka |
| 2010/0076208 A1* | 3/2010 | Dhingra ............... B01J 23/52 |
| | | 549/533 |
| 2014/0262743 A1 | 9/2014 | Landry et al. |
| 2016/0271588 A1* | 9/2016 | Kobiro ............... B01J 23/462 |
| 2016/0346763 A1* | 12/2016 | Wahab ............... B01J 21/063 |

OTHER PUBLICATIONS

Negishi et al., enhanced photocatalytic water splitting using gold nanoclusters on titania, (Nanoscale(2013), 5(16), 7188-7192).*
PCT International Search Report No. PCT/AU2016/051175, dated Mar. 14, 2017.
Wilaiwan Chanmanee et al., "Solar Photothermochemical Alkane Reverse Combustion", Department of Chemistry and Biochemistry, University of Texas at Arlington and Department of Mechanical and Aerospace Engineering, Unversity of Texas at Arlington, Jan. 21, 2016, pp. 1-6.
Zhang, Qin-Hui et al., "Photocatalyctic reduction of C02 with H20 on Pt-loaded Ti02 catalyst", Aug. 18, 2009, pp. 335-340.
V. Jeyalakshmi et al., "Application of photo catalysis for mitigation of carbon dioxide", Nov. 21, 2012, pp. 2565-2602.
Jan-Yves Rizicka et al., "Toward Control of Gold Cluster Aggregation on Ti02 via Surface Treatments", Oct. 1, 2015, pp. 24465-24474.

* cited by examiner

PHOTOCATALYTIC CONVERSION OF CARBON DIOXIDE AND WATER INTO SUBSTITUTED OR UNSUBSTITUTED HYDROCARBON(S)

CROSS REFERENCE TO RELATED APPLICATIONS

This application is a § 371 national stage of PCT International Application No. PCT/AU2016/051175, filed Nov. 30, 2016, which claims priority to AU2015904952, filed Nov. 30, 2015, the contents of which is incorporated herein in its entirety by this reference

FIELD

The present invention relates to the production of hydrocarbon(s) such as methane or substituted hydrocarbon(s) such as methanol. In one embodiment, the hydrocarbon(s) can be formed using water and carbon dioxide as precursor materials.

BACKGROUND

For many decades, oil has been the main feed stock for the production of hydrocarbons. Recently, however, concerns over increases in costs of fossil fuels and the effect of global warming have prompted the exploration of alternative more renewable feed stocks.

Carbon dioxide has received much attention as an alternative feed stock for the production of methane, because there is a drive to reduce carbon dioxide emissions to help slow global warming, and because it is cheap and readily available. Carbon dioxide can be converted into hydrocarbons such as methane by reacting it with hydrogen, for example via the Sabatier reaction. The hydrocarbons produced can then be converted into other forms such as methanol.

While the process of converting carbon dioxide into hydrocarbons is relatively well understood, it has been an energy intensive process. For example, the hydrogen used for carbon dioxide conversion is usually produced from fossil fuels by steam reforming, and conversion of carbon dioxide to hydrocarbons typically requires relatively high temperatures. Catalysts are often employed to increase efficiencies, but they can add significant costs to the process. Using fossil fuels to produce hydrogen, which is then converted back into hydrocarbons, is known to be a relatively inefficient process. Alternative hydrogen feed stocks, such as water, can be used, but their use is a relatively energy intensive process.

Accordingly, there is a need to find a more sustainable way of producing hydrocarbons using more efficient and environmentally friendly methods.

SUMMARY OF DISCLOSURE

According to a first aspect of the present invention there is provided a method for the production of hydrocarbon(s), such as methane, or substituted hydrocarbons, such as methanol, the method comprising the steps of:
  contacting a catalyst with water and carbon dioxide in the presence of light in order to photocatalyse:
    (i) the splitting of at least some of the water into hydrogen and oxygen; and
    (ii) the reaction between hydrogen and carbon dioxide to produce hydrocarbon(s), such as methane, and/or substituted hydrocarbons, such as methanol;
  wherein the catalyst comprises at least gold and ruthenium, in the form of at least one nanocluster supported by a support substrate such as a titanium dioxide substrate.

According to a second aspect of the invention, there is provided a method for the production of hydrocarbon(s), such as methane, or substituted hydrocarbons, such as methanol, the method comprising the steps of:
  a. contacting a first catalyst with water in order to photocatalyse the splitting of at least some of the water into hydrogen and oxygen;
  b. contacting a second catalyst with a gas stream comprising carbon dioxide and hydrogen, at least some of the hydrogen can be produced from step (a), in order to photocatalyse the reaction between the hydrogen and carbon dioxide to produce hydrocarbon(s), such as methane, and/or substituted hydrocarbons, such as methanol.

The first and second catalyst can be the same catalyst. The first catalyst and the second catalyst can be different catalysts. The first and second catalysts can comprise one or more nanoclusters. The first and second catalysts can be immobilized on the support. The first and second catalysts can be activated on the support. The nanoclusters can comprise gold and/or ruthenium nanoclusters. The nanoclusters can have an average cluster size of less than about 2 nm.

It should be understood that the splitting of at least some of the water into hydrogen and oxygen can include splitting the water into hydrogen and or oxygen containing species such as hydrogen radicals, hydronium and or hydroxyl radicals.

Without wishing to be limited by hypothesis or theory, embodiments of the invention will now be summarised and then described based on the understanding of how the catalyst performs under various conditions.

A. Embodiments in which there is a First Catalyst and a Second Catalyst

According to a third aspect of the present invention there is provided a method for the production of hydrocarbon(s), such as methane, or substituted hydrocarbons, such as methanol, the method comprising the steps of:
  a. contacting a first photocatalyst with water in the presence of light in order to photocatalyse the splitting of at least some of the water into hydrogen and oxygen;
    wherein the first photocatalyst comprises gold nanoclusters supported by a titanium dioxide substrate;
  b. contacting a second catalyst with a gas stream comprising carbon dioxide and at least some of the hydrogen produced from step (a) in order to catalyse the reaction between the hydrogen and carbon dioxide to produce hydrocarbon(s), such as methane, and/or substituted hydrocarbons, such as methanol;
    wherein the second catalyst comprises ruthenium nanoclusters supported by a titanium dioxide substrate.

In an embodiment, the catalyst can comprise a first catalyst and a second catalyst. The first catalyst can be a photocatalyst. The second catalyst can be a photocatalyst.

Step (a): A First Catalyst for the Photocatalytic Splitting of Water into Hydrogen and Oxygen The first photocatalyst preferred for use in step (a) above can comprise a substrate and an active metal component. The substrate can be graphene, graphite, carbon black, nanotubes, fullerenes, and/or zeolites. The substrate can be a carbon nitrate CxNy. The substrate can be a metal oxide or nitride. The substrate can be a titania, silica and/or alumina. The substrate can be barium titanate or perovskite. The substrate can be a titanium oxide. The titanium oxide support substrate can include anatase and/or the commercially available P25. The substrate can be a monolithic. The substrate can have a planar surface such as a plate or disc. The substrate can be particulate. The substrate can comprise nanoparticles. In one embodiment, the substrate comprises titanium dioxide nanoparticles.

Photocatalysts are activated by light. The light used can be determined by the specific type of photocatalysts. For example, some photocatalysts can catalyse a reaction using light with a wavelength over a broad range, while others may only catalyse the reaction with a specific wavelength e.g. 365=/±5 nm or 400±5 nm. Depending on the reaction, it may be advantageous that the first photocatalyst comprises two or more types of photocatalyst where one can perform at a specific wavelength and the other can perform over a broad wavelength range Usually, the more intense the light, the more efficient the catalytic process is. However, in some circumstance the reactants and/or products may be degraded if the light source is too intense. Therefore, it can be advantageous to have a balance between rate of catalysis and the rate of degradation of the reactants/products.

A common wavelength range for photocatalysts are those in the ultraviolet range i.e. 200-400 nm. The source of ultraviolet light may be from a dedicated lamp or may be from a natural light source, such as the sun. Usually commercial ultraviolet light sources have a greater Intensity compared to natural sources. Natural light sources can have a UV intensity (i.e. <400 nm) of approximately 4.63 mW cm$^{-2}$, while commercial sources can be many times more intense, such as >1000 mW cm$^{-2}$. Using a natural light source can be advantageous from an energy Input perspective, and can make the process more environmentally friendly. If a natural light source is used, it may be supplemented with a commercial light source. Such circumstances may include during times of inclement weather and/or during times of reduced light activity, such as at night. In areas with plentiful natural light, e.g. Australia, it may be advantageous to rely on the sun as a source of ultraviolet light during the day and a commercial light source during the night to allow constant photocatalytic activity over a 24 hour period. Concentrated solar sources, can provide energies in the range of from about 500 to about 1000 suns i.e. 2315-4630 mW/cm$^{-2}$.

An advantage of using photocatalysts (when compared to other types of catalysts) is that they often do not require the use of heat to catalyse reactions. Not requiring heat can decrease operational costs, make the production of hydrogen more environmentally friendly, and make the production of hydrogen safer. Temperatures that can be used for photocatalysis are around room temperature e.g. about 20-30° C., but may be as high at about 100-300° C., for example 250° C. Nevertheless, the photocatalyst could be used with the addition of heat, which may allow for a reduction in light energy input.

The active metal of the photocatalyst can be selected from gold, silver, copper, platinum, palladium, nickel, rhenium, ruthenium and/or titanium, and/or other transition metals and their corresponding oxides. In a embodiment the active metal is gold. It may be advantageous to have more than type of active metal, one of which could be gold. Whilst gold is exemplified herein, it should be understood that the invention is not so limited and other active metal nanoclusters could be prepared using the details disclosed herein.

The form in which the active metal is associated with the substrate can be determined by the reaction and/or the reaction conditions of the formation of the photocatalyst. For example, the active metal(s) could be present in the form of complexes, nanoparticles and/or clusters/nanoclusters. It may be advantageous to have more than one active metal where each metal has a different form. In a preferred embodiment, the active metal is present as a nanocluster.

By way of background, metal complexes have an active metal that is surrounded by one or more ligand(s). The type of ligand(s) can greatly affect the performance of the catalyst. One of the ligands can be immobilised on the surface of the substrate, which can help to prevent the complex from disassociating from the substrate. This can be advantageous, for example, in helping to recover the photocatalyst once a reaction is complete. Nanoparticles, on the other hand, can have an average size in a range of from about 5 to about 100 nm. The shape and arrangement of the nanoparticles can greatly affect the function as a photocatalyst. For example, a nanoparticle with a cuboid shape usually has a lower surface area compared to nanoparticles that are rods or ribbons, and a lower surface area is usually associated with a decrease in catalyst efficiency. Clusters or nanoclusters (referred to herein interchangeably unless the context makes clear otherwise), in yet a further form, refer to a collection or group of two or more active metal atoms, but usually contain less than approximately 200 atoms. Clusters typically differ from nanoparticles both structurally and electronically—unique packing of atoms not seen in larger metal particles and non-plasmonic (Au/Ag)/metallic. It terms of size, nanoclusters are usually considered as being between complexes and nanoparticles. It is to be understood that the number of atoms used to describe a nanocluster is the average number and there is typically a distribution associated with the average number. For example, nanoclusters containing more than 20 metal atoms can have a distribution of ±10 or more percent e.g. M30±3, MSS5, M100±10. The metals that comprise the nanoclusters can comprise ligands. Similar to complexes, any ligands associated with the nanocluster can be used to stabilise the nanocluster and in some circumstances may help to improve the performance of the nanocluster when as a catalyst. In some cases, it is preferred to remove any ligands before the compound is used as a photocatalyst.

The first photocatalyst can have a support that is photoactive. The clusters can be deposited onto a support capable of adsorbing light of appropriate wavelength. The cluster plus the photoactive support forms the photocatalyst. The support can be particulate itself or is can be a bulk solid substrate. The bulk solid substrate can be a wafer such as a silicon wafer or a porous silica disk. The first photocatalyst in the form of a paste can be applied to the support. The thickness of the applied photocatalyst can be varied.

In one embodiment, the photocatalyst comprises a titanium dioxide substrate in the form of nanoparticles; the nanoparticles are associated with gold nanoclusters. The gold nanoclusters can comprise $Au_3$ to $Au_{101}$. The gold dusters can be selected from $(Ph_3Pau)_3OBF_4$, $[(AuPPh_3)_3O]PF_6$, $Au_5(PPh_3)_4Cl$, $Au_6(PPh_3(BF_4)_2$, $Au_6(PPh_3MNO_3)_2$, $Au_6(PPh_3)_6(PF_6)_2$, $Au_8(PPh_3)_8(NO_3)_2$, $Au_8(PPh_3)_7(NO_3)_2$, $Au_9(PPh_3)_8(NO_3)_3$, $Au_{10}(PPh_3)_5(C_6F_5)_4$, $Au_{11}Cl_3\{(m-CF_3C_6H_4)_3P\}_7$, $Au_{11}(PPh_3)_7(PF_6)_3$, $[Au_{13}(Pme_2Ph)_{10}Cl_2](PF_6)_3$, $Au_{13}(PPh_3)_4[S(CH_2)_{11}(CH_3)]_4$, $[Au_{13}(PPH_2CH_2PPH_2)_6](NO_3)_4$, $Au_{55}$ (PH$_2$PC$_6$H$_4$SO$_3$Na.2H$_2$O)$_{12}$ Cl$_6$, Au$_{55}$(PPh$_3$)$_{12}$Cl$_6$, Au$_{101}$(PPh$_3$)$_{21}$Cl$_5$, where "Ph" is phenyl and "Me" is methyl.

Once the size of the nanoclusters begins to increase over approximately 2 nm, the activity of the photocatalyst may decrease. In an embodiment, the nanoclusters have an average size of less than about 2.5, 2, 1.5 or 1 nm. For example, the average size of e.g. Au$_{101}$ can be approximately 1.6 nm.

The number of nanoclusters per substrate nanoparticle may depend on the type of active metal used. In one embodiment, the number of nanoclusters per nanoparticle is at least about 1, 2, 5, 10, 15, 20, 15 or 30. The percentage approximate coverage of the nanoparticles with nanoclusters can be in the range of from about 0.1 to about 10% or more, or at least about 0.1, 0.5, 1, 1.7, 2, 3, 4, 5, 6 or 10% or more as a percentage of the total available surface area. In one embodiment, the approximate coverage of the nanoparticles with gold nanoclusters is in the range of from about 0.17 to about 1.7 wt %.

The first photocatalyst can be pre-treated prior to use. Treatment methods can include calcining and/or acid treatment. Acid treatment can be performed with or without calcining. Where calcining is used, acid treatment can be performed before or after calcining. It is thought that acid treatment has an effect on the interaction between the catalyst substrate and the active metal during preparation of the photocatalyst.

Calcining can be performed at a temperature of at least about 50, 100, 200, 300 or 400° C. to remove any residual carbon contamination from the photocatalyst surface. Calcining can be performed under oxygen and/or hydrogen atmospheres and/or under vacuum. There is thought to be an improvement in H$_2$ gas production as the first photocatalyst is treated under successively harsher conditions. This may be due to the removal of any ligands from the photocatalyst surface (leaving only the active metal clusters behind). It is hypothesised that in some embodiments, the removal of ligands and an increase in cluster size improves the catalytic performance of anatase-supported Au clusters.

To help ensure all contaminates (including adventitious carbons) are removed from the first photocatalyst prior to use, it can be advantageous to expose the first photocatalyst to a vacuum for an extended prior of time. Prior to use the first photocatalyst can be held under vacuum for at least about 1, 2, 5, 10, 12 or 15 hours. It is preferred that the photocatalyst is not exposed to the atmosphere once it has been held under vacuum.

The step of contacting the first photocatalyst with water can involve exposing all or some of the surface(s) of photocatalyst with water in order to effect a reaction. The water can be from any source. The water can be substantially pure, or it can be a part of an aqueous solution. The water used to produce hydrogen can be in liquid form and/or vapour form. In one embodiment, the step of contacting the photocatalyst with water comprises immersing the photocatalyst in a body of water. The water can flow over the first photocatalyst. The flow can be continuous. When liquid water is used, the first photocatalyst may be homogenously or heterogeneously distributed in the body of water. Homogenous distribution may be performed by vigorously mixing the body of water and a first photocatalyst in a fine particulate form. The first photocatalyst can be an aggregate that can easily be separated from the body of water. Heterogeneous distribution may be achieved by immobilising the first photocatalyst on at least one stationary support. In one embodiment, the first photocatalyst is supported on rods that can be inserted into the body of water.

In one embodiment, the step of contacting the first photocatalyst with water Includes allowing a water vapour to come into contact with the first photocatalyst. Bringing the water vapour into contact with the first photocatalyst can be performed in a variety of ways, for example, continuously flowing water vapour over the first photocatalyst. The pressure of the water vapour can be varied to achieve the desired result (optimum hydrogen production). Condensation of water vapour can occur if the pressure of the vapour is too high. To prevent condensation, the heat of the vapour may be increased, but applying too much heat to prevent condensation may be undesirable. The water vapour may be provided at below atmospheric pressures. In an embodiment, step (a) is performed under 20 Torr of water vapour. Additional gases may be included with the water vapour. The additional gas may be an inert gas. The inert gas can be argon (Ar). In one embodiment, step (a) s performed under 280 Torr of argon (Ar).

During the production of hydrogen, oxygen is also produced according to the following equation (1):

$$2H_2O \rightarrow 2H_2 + O_2 \quad (1).$$

It can be advantageous to remove either hydrogen and/or oxygen to drive the reaction through favourable thermodynamics. The hydrogen and oxygen gases can be collected and stored for use in a subsequent reaction. The subsequent reaction can be the reaction of at least some of the hydrogen with carbon dioxide in an e.g. 4:1 molar ratio of hydrogen to carbon dioxide to produce hydrocarbons such as methane. In one embodiment, all of the hydrogen is passed to a further reaction to assist in the production of methane.

The amount of hydrogen that can be produced in step (a) can be at least about 15, 50, 80, 100, 150, 200, 250, 350, 450, 550, 1000, 1500, 2000 or 5000 µmol hr$^{-1}$ g$^{-1}$ cm$^{-2}$.

Step (b): A Second Catalyst for the Catalytic Reaction of Carbon Dioxide and Hydrogen The hydrogen produced in step (a) can be used as feed for the production of unsubstituted hydrocarbons. Hydrocarbons can include C$_1$ to C$_{10}$ containing compounds such as methane, ethane, propane, butane, pentane, hexane, heptane, octane, nonane, decane, their various isomeric forms such as n-, iso-, sec- and tert-alkanes, and their respective oxides such as methanol and ethanol. More complex hydrocarbons such as aromatics may also be produced. The hydrocarbons produced can be greater than C$_{10}$. The hydrogen can also be used as a feed for the formation of a substituted hydrocarbon such as methanol, ethanol, propanol, and so on.

Hydrogen can be converted into methane using the Sabatier reaction shown in equation (2):

$$CO_2 + 4H_2 \rightarrow CH_4 + 2H_2O \quad (2)$$

Hydrogen can be converted into methanol using the following equation (3):

$$CO_2 + 3H_2 \rightarrow CH_3OH + H_2O \quad (3).$$

Industrially, it is understood that these processes require the use of high temperatures i.e. about 200 to 500° C. and typically they require the presence of copper-, zinc oxide- and/or alumina-based catalysts.

The step of contacting the second catalyst with carbon dioxide and hydrogen can involve allowing the gas streams to flow over the surface. The amount of gas introduced to the surface of the second photocatalyst can be controlled (in terms of molar ratio) so as to ensure the desired reaction product. Steps (a) and (b) can be undertaken sequentially as two separate method steps, or they can be undertaken concurrently.

The second catalyst can be a photocatalyst. The photocatalyst can be activated by UV wavelengths of light. The second catalyst preferred for use in step (b) can comprise a substrate and an active metal component. The substrate can be as described above e.g. graphene, graphite, carbon black, nanotubes, fullerenes, and/or zeolites. The substrate can be an oxide or a nitride. The substrate can be titania, silica and/or alumina and their oxides. The substrate can be a titanium oxide. The titanium oxide support can include anatase and/or the commercially available P25. The substrate can be a planar surface or it could be particulate. The substrate can comprise nanoparticles. In one embodiment, the substrate comprises titanium dioxide nanoparticles.

The active metal of the photocatalyst of step (b) can be selected from gold, copper, silver, platinum, palladium, nickel, rhenium, ruthenium and/or titanium, and/or other transition metals and their corresponding oxides and/or other transition metals and their corresponding oxides. In an embodiment the active metal is ruthenium. It may be advantageous to have more than type of active metal. where at least ruthenium is present.

The second catalyst can be applied to a support. The support can be a particulate to increase the surface area, or the support can be solid substrate. The solid substrate can be a wafer such as a silicon wafer or a porous silica disk. The second catalyst can be applied to the support as a layer. The thickness of the layer can be varied.

The form in which the active metal is supported on the substrate can be determined by the reaction and/or the reaction conditions. For example, the active metal(s) may be present in forms of complexes, nanoparticles and/or nanoclusters. These forms of active metal are described in relation to step (a) above and that description also applies here. It may be advantageous to have more than one active metal, with each metal having a different form i.e. nano clusters and complexes. In an embodiment, the active metal is present as a ruthenium nanocluster.

In one embodiment, the second catalyst comprises a titanium dioxide substrate in the form of nanoparticles associated with ruthenium nanoclusters. The percentage of ruthenium nanoclusters loaded onto the nanoparticles can be at least about 0.1, 0.2, 0.5, 1, 2, 5 or 10 wt %.

The second catalyst can be pre-treated prior use. Treatment methods can Include calcining and/or acid treatment. To help ensure contaminates are removed from the catalyst prior to use, it can be advantageous to expose the catalyst to a vacuum for an extended prior of time. Calcining can be performed for a period of at least about 1, 2, 5, 10, 12 or 15 hours. The pre-treatment can be at a temperature of at least about 50, 100, 200, 300 or 400° C. to remove any residual carbon contamination from the photocatalyst surface. Calcining can be performed under oxygen and/or hydrogen atmospheres and/or under vacuum. This may be due to the removal of any ligands from the photocatalyst surface (leaving only the active metal clusters behind). It is hypothesised that in some embodiments, the removal of ligands and an increase in particle size improves the catalytic performance of anatase-supported Ru clusters.

A ruthenium-based catalyst may significantly reduce the temperatures and/or pressures required to produce methane and/or methanol. For example, temperatures less than about 100, 200 or 250° C. with pressure below a few atmospheres can be used with ruthenium-based catalysts to produce hydrocarbons (substituted or unsubstituted) from hydrogen. The efficiency of a ruthenium-based photocatalyst may also be improved by exposure to ultraviolet light. The support may assist in the photocatalytic production of hydrocarbon or substituted hydrocarbons.

The amount of methane that can be produced in step (b) can be at least about 350, 450, 550, 1000, 2000 or 5000 μmol $hr^{-1} g^{-1} cm^{-2}$.

Apparatus and System

The reaction of steps (a) and (b) may be performed in an apparatus (a reactor). The apparatus for step (a) can have an inlet for the introduction of water. The first photocatalyst of step (a) may be housed in a part of the apparatus and arranged so that the water can come Into contact with the surface of the first photocatalyst. In some embodiments, the apparatus Is sealable once the water has been Introduced. The water can be Introduced as a liquid or vapour. If the water Is a vapour it can be introduced under pressure. A light source can be arranged Inside or outside of the vessel to allow activation of the first photocatalyst. The reaction may be allowed to proceed for as long as is necessary to produce as much hydrogen as is required (or as is stoichiometrically possible). The temperature and/or pressure within the reactor may be slowly increased to effect the optimal reaction. The gases evolved in the reactor may be collected from the apparatus from an outlet. The gases may be collected and separated.

A second apparatus may be provided for step (b). In step (b) carbon dioxide and hydrogen are mixed at the desired molar ratio in the presence of a second photocatalyst. The second photocatalyst may be housed in a part of the apparatus and arranged so that the gas streams can come into contact with the surface of the photocatalyst. In some embodiments, the apparatus is sealable once the gases have been introduced. A light source can be arranged inside or outside of the vessel to allow activation of the second photocatalyst. The reaction may be allowed to proceed for as long as is necessary to produce as much product as is required. The temperature and/or pressure may be slowly increased in the apparatus to effect reaction. The gases evolved may be collected from the apparatus from an outlet. The gases may be collected and separated. In step (a) and step (b) the apparatus can be an autoclave.

In one embodiment step (a) and step (b) are performed in the same apparatus. Because the production of hydrogen is photocatalytic, it may be possible to employ both the first photocatalyst and the second photocatalysts to produce both hydrogen and hydrocarbons at the same time, sequentially. The two photocatalysts, first and second, may be independent of each other, or they may be associated. If the two catalysts are associated with each other, it may be that, for example, gold clusters and ruthenium nanoclusters are supported on the same titanium dioxide support. In some embodiments, there are gold ruthenium nanoclusters as described further below. Having one support with two active nanoclusters or one support with active Au—Ru nanoclusters may reduce the operational costs of the production of hydrocarbons and may make the process more environmentally friendly.

In step (a) the molar ratio of hydrogen to carbon dioxide is always greater for any carbon dioxide produced during the production of hydrogen. As the molar ratio of hydrogen to carbon dioxide in Eq. 2 and Eq. 3 is always greater than 1:1, any carbon dioxide produced during the production of hydrogen is preferably supplemented with an additional source of carbon dioxide. If the production of hydrocarbons is coupled with a production that burns hydrocarbons e.g. for electricity, then the products from one process may be a feed stock for another.

B. Embodiments in which there is a Single Catalyst

In this embodiment, it is thought that steps (a) and (b) occur at the same catalyst site. The method of the present invention can be undertaken in the presence of a catalyst which can
(i) split at least some of water (into hydrogen and oxygen); and
(ii) react hydrogen and carbon dioxide to produce hydrocarbon(s), such as methane, and/or substituted hydrocarbons, such as methanol;

The catalyst can comprise a substrate and an active metal component. The substrate can be as described above with respect to the other catalysts. The substrate can be e.g. graphene, graphite, carbon black, nanotubes, fullerenes, and/or zeolites. The substrate can be titania, silica and/or alumina. The substrate can be a titanium oxide. The titanium oxide support substrate can include anatase and/or the commercially available P25. The substrate can be monolithic. The substrate can have a planar surface such as a plate or disc. The substrate can be particulate. The substrate can comprise nanoparticles. In one embodiment, the substrate comprises titanium dioxide nanoparticles.

The catalyst can be a photocatalyst that is activated by light. A common wavelength range for photocatalysts are those in the ultraviolet range i.e. 200-400 nm e.g. 365 nm=/±5 nm. The source of ultraviolet light may be from a dedicated lamp or may be from a natural light source, such as the sun. Photocatalysts are described above, and all description made there applies here unless the context makes clear otherwise. An advantage of using photocatalysts (when compared to other types of catalysts) is that they often do not require the use of heat to catalyse reactions. Not requiring heat can decrease operational costs, make the production of hydrogen more environmentally friendly, and make the production of hydrogen safer. Temperatures that can be used for photocatalysis are around room temperature e.g. about 20-30° C., but may be as high at about 100-300° C., for example 250° C. Nevertheless, the photocatalyst could be used with the addition of heat, which may allow for a reduction in light energy input.

The active metal of the catalyst can be selected from one or more of gold, copper, silver, platinum, palladium, nickel, rhenium, ruthenium and/or titanium, and/or other transition metals and their corresponding oxides. In an embodiment the active metal comprises only ruthenium. In an embodiment, the active metals comprise gold and ruthenium. The active metal can comprise gold and ruthenium bound together. The gold and ruthenium can have a bond distance in the range of from about 2.5 to 3 Å. such as 2.7 to 2.8 Å, or at least about 2.5, 2.7, 2.8 or 3 Angstrom (Å). The gold x to ruthenium y ratio can be about 1:1.5, 1:2, 1:3. The active metal can be $AuRu_3$, $Au_2Ru_3$ and or $Au_2Ru_4$. The $AuRu_3$ can be $Ru_3AuPPh_3Cl(CO)_{10}$. The $Au_2Ru_3$ can comprise $[Au_2Ru_3 (\mu-H) (\mu_3-COMe) (\mu-L_2) (CO_9)]$ {where $L_2=Ph_2P(CH_2)PPh_2$}. The $Au_2Ru_4$ can comprise $[Au_2Ru_4 (\mu-H) (\mu-H) (\mu-Ph_2ECH_2E'Ph_2) (CO)_{12}]$ {where E=E'=As or P; E=As, E'=P} and or $[Au_2Ru_4 (\mu_3-H) (\mu-H) (\mu-1,2-Ph_2PC_6H_4PPh_2) (CO)_{12}]$ and or $[Au_2Ru_4 (\mu_3-H) (\mu-H) (\mu-dppf) (CO)_{12}]$ {where dppf=1,1'-bls(diphenylphosphino)ferrocene}. Sourced from: "Metal Clusters in Chemistry: Vol 1 Molecular Metal Clusters", Editors: P. Braunstein, L. A. Oro, P. R. Raithby. Wiley-VCH 1999. ISBN: 3-527-29549-6, the contents of which is incorporated in so far as the AuRu metal clusters are described and unless the context makes clear otherwise.

The active metal can be present in the form of complexes, nanoparticles and/or clusters/nanoclusters. In a preferred embodiment, the active metals are present as a nanocluster. Clusters or nanoclusters (referred to herein interchangeably unless the context makes clear otherwise), in yet a further form, refer to a collection or group of two or more active metal atoms, but usually contain less than approximately 200 atoms. It terms of size, nanoclusters are usually considered as being between complexes and nanoparticles. The nanocluster can comprise more than 20 metal atoms with a distribution of ±10 or more percent e.g. $M_{30}±3$, $M_{55}±5$, $M_{100}±10$. The metals that comprise the nanoclusters can comprise ligands. Similar to complexes, any ligands associated with the nanocluster can be used to stabilise the nanocluster and in some circumstances may help to improve the performance of the nanocluster when as a catalyst. In an embodiment, the nanocluster with ligands is of the formula $Ru_3(\mu-AuPPh_3)(\mu-Cl)(CO)_{10}$. In some cases, it is preferred to remove any ligands before the compound is used as a catalyst. In some embodiments, the ligands assist in the catalytic activity.

Once the size of the nanoclusters begins to increase over approximately 2 nm, the activity of the photocatalyst may decrease. In an embodiment, the nanoclusters have an average size of less than about 2.5, 2, 1.5 or 1 nm. An active site for reaction can comprise more than one or more nanoclusters.

The catalyst can be applied to a support. The support can be particulate itself or can be a solid substrate. The solid substrate can be a wafer such as a silicon wafer or a porous silica disk. The first catalyst in the form of a paste can be applied to the support. The thickness of the applied catalyst can be varied. The nanoclusters can be supported by e.g. titanium dioxide nanoparticles. The number of nanoclusters per substrate nanoparticle may depend on the type of active metal used. In one embodiment, the number of nanoclusters per nanoparticle is at least about 1, 2, 5, 10, 15, 20, 15 or 30. The percentage approximate coverage of the nanoparticles with nanoclusters can be at least in the range of from about 0.1 to 10% or more, or about 0.1, 0.5, 1, 1.7, 2, 3, 4, 5, 6 or 10% or more as a percentage of the total available surface area.

In an embodiment, the method can comprise contacting a photocatalyst with water and $CO_2$ in order to photocatalyse the reaction of water with CO2, wherein the photocatalyst comprises gold nanoclusters and ruthenium nanoclusters or mixed gold-ruthenium nanoclusters supported by a titanium dioxide substrate.

The catalyst can be pre-treated prior to use. Treatment methods can include calcining and/or acid treatment. Acid treatment can be performed with or without calcining. Where calcining is used, acid treatment can be performed before or after calcining. It is thought that acid treatment has an effect on the interaction between the catalyst substrate and the active metal during preparation of the catalyst.

Heterogeneous catalysts and photocatalysts are generally pre-treated in situ before testing, in order to remove advantageous hydrocarbons and other surface-adsorbed species, or to open up catalyst active sites by removal of ligands. Many different techniques for this can be undertaken for example including ozone treatment, calcination in $O_2$ or $H_2$, and heating under a flow of inert gas. Preferably, any treatment does not have any damaging effect upon active metal clusters which might cause them or the substrates to which they are attached to aggregate into larger nanoparticles. The selection of an appropriate pre-treatment which removes adsorbed contaminants while still retaining intact clusters upon the surface for these materials is preferred. Calcining can be performed under oxygen and/or hydrogen atmospheres and/or under vacuum. Calcining can be performed at a temperature of not more than about 50, 100, 200, 300 or 400° C. In an embodiment, the calcining is undertaken at about 200° C. under vacuum. There is thought to be improvement in $H_2$ gas production as the catalyst is treated under successively harsher conditions. This may be due to the removal of any ligands from the catalyst surface (leaving only the active metal clusters behind). It is hypothesised that in some embodiments, the removal of ligands and an increase in particle size improves the catalytic performance of anatase-supported clusters.

To help ensure all contaminates (including adventitious carbons) are removed from the catalyst prior to use, it can be advantageous to expose the catalyst to a vacuum for an extended prior of time. Prior to use the catalyst can be held under vacuum for at least about 1, 2, 5, 10, 12 or 15 hours. It is preferred that the catalyst is not exposed to the atmosphere once it has been held under vacuum.

The step of contacting the catalyst with water can involve exposing all or some of the surface(s) of catalyst with water in order to effect a reaction. The water can be from any source and the various ways in which the surface of the catalyst can contact water are described above, and also apply here unless the context makes clear otherwise. The catalyst is also exposed to carbon dioxide. Preliminary testing indicates a $P_{CO2}:P_{H2O}$ ratio of about 2, 3 or 4 is optimal for solar fuel production. In an embodiment, the $P_{CO2}:P_{H2O}$ ratio is 3. In some embodiments, optimal production of CO and $H_2$ was observed at a reagent ratio of 1:1, and $CO_2:H_2O$ ratios in the range of at least about 0.5 to 4, preferably about 1 to about 3, give peak hydrocarbon production.

During the production of hydrogen, oxygen is also produced according to the following equation (1):

$$2H_2O \rightarrow 2H_2 + O_2 \qquad (1).$$

The hydrogen can be used for the production of unsubstituted hydrocarbons. Additional hydrogen can be injected into the system if desired. Hydrocarbons can include $C_1$ to $C_{10}$ containing compounds such as methane, ethane, propane, butane, pentane, hexane, heptane, octane, nonane, decane, their various isomeric forms such as n-, iso-, sec- and tert-alkanes, and their respective oxides such as methanol and ethanol. More complex hydrocarbons such as aromatics may also be produced. The hydrocarbons produced can be greater than $C_{10}$. The hydrogen can also be used for the formation of a substituted hydrocarbon such as methanol, ethanol, propanol, and so on.

Hydrogen can be converted into methane using the Sabatier reaction shown in equation (2):

$$CO_2 + 4H_2 \rightarrow CH_4 + 2H_2O \qquad (2)$$

Hydrogen can be converted Into methanol using the following equation (3):

$$CO_2 + 3H_2 \rightarrow CH_3OH + H_2O \qquad (3).$$

It may be that the catalyst is able to stabilise intermediaries in reaction (1) such as hydrogen radicals, hydronium and or hydroxylradicals that go on to react with $CO_2$.

The amount of hydrogen that can be produced by the Au—Ru catalyst can be at least about 70, 80, 90 or 100 μmol $hr^{-1}$ $g^{-1}$ $cm^{-2}$. The amount of methane, ethane, ethene, propane and/or propene that can be produced in step (b) can be at least about 350, 450, 550, 1000, 2000 or 5000 nmol $hr^{-1}$ $g^{-1}$ $cm^{-2}$.

Apparatus and System

The reaction of steps (a) and (b) may be performed in an apparatus (a reactor). The apparatus can have an inlet for the introduction of water. The catalyst may be housed in a part of the apparatus and arranged so that the water can come into contact with the surface of the catalyst. In some embodiments, the apparatus is sealable once the water has been introduced. The water can be introduced as a liquid or vapour. If the water is a vapour it can be introduced under pressure. A light source can be arranged inside or outside of the vessel to allow activation of the catalyst. The temperature and/or pressure within the reactor may be slowly increased to effect the optimal reaction. The apparatus can have an inlet for the introduction of carbon dioxide. The catalyst may be housed in a part of the apparatus and arranged so that the carbon dioxide can come into contact with the surface of the catalyst. In some embodiments, the apparatus is sealable once the carbon dioxide has been introduced. Alternatively the carbon dioxide is continuously introduced into the apparatus. The reaction temperature can be elevated to at least about 120, 150, 180 or 200° C. The gases evolved in the reactor may be collected from the apparatus from an outlet. The gases may be collected and separated.

According to a second aspect of the invention there is provided an apparatus for the production of hydrocarbon(s) such as methane or substituted hydrocarbons such as methanol, the apparatus adapted to undertake the method described herein.

According to a third aspect of the invention there is provided hydrocarbons or substituted hydrocarbons when produced by a method as described herein, or when produced in an apparatus herein described. According to a fourth aspect of the invention there is provided a catalyst when used in the method or apparatus of the invention.

BRIEF DESCRIPTION OF FIGURES

Embodiments of the invention will now be described, by way of example only, with reference to the accompanying non-limiting drawings, in which.

EXAMPLES OF EMBODIMENTS OF THE INVENTION

Embodiments of the invention, and other embodiments, will now be described with reference to the accompanying non-limiting examples. Any % referred to herein may be wt % unless the context makes clear otherwise.

Example 1 Formation of the Gold Nonoclusters

An aqueous stock solution of 50 mM gold chloride anions ($AuCl_4^-$) in a glass vial was made by dissolving $HAuCl_4$ $3H_2O$ with the same molar amount of HCl, ensuring stability for more than several months. An aqueous stock solution of 50 mM borohydride anions ($BH_4^-$) in a glass beaker was made by dissolving $NaBH_4$ granules with the same molar amount of NaOH, guaranteeing stability for several hours at room temperature.

For the smallest nanoparticles of 3.2 nm in diameter, we added 100 μL of the $AuCl_4^-$/H solution to a glass vial with water and later injected 300 μL of the $BH_4^-$/$OH^-$ solution all at once, while stirring on a mechanical shaker for uniform mixing. The total weight of the aqueous solution was controlled to be 10 g so that the concentration of gold ions is 0.50 mM. The solution changed colour from light yellow to orange immediately, and then to red while the vial was stirred for 1 min to release hydrogen gas molecules. For nanoparticles of other sizes, the amount of the $BH_4^-$/$OH^-$ solution was increased from 300 to 650 uL followed by heating for 2-3 min at the boiling temperature of water on a hot plate. The average diameter of gold nanoparticles was precisely controlled from 3.2 to 5.2 nm. The amount of the $BH4^-$/$OH^-$ solution was changed from 200 to 1300 μL during the search for the "sweet zone" before heating.

Nanoparticles can be prepared by this method as described in the paper entitled: Charged Gold Nanoparticles in Non-Polar Solvents 10 Minute Synthesis and 2D Self-Assembly, LANGMUIR, 26(10) pp 7410-7417 (2010), the entire contents of which are hereby incorporated by reference in their entirety. If there are any inconsistencies between this document and the incorporated document, this document shall take precedence unless the context makes clear otherwise.

Example 2 Photocatalytic Performance of Pt—$TiO_2$ for Water-Splitting (Step (a))

In order to establish a benchmark (control) for photocatalytic experiments of Au/$TiO_2$, photocatalytic water-splitting experiments were undertaken using platinised P25 nanoparticles (1.0 wt % Pt/Ti $O_2$) and platinised anatase nanoparticles (1.0 wt % Pt/anatase).

In addition, various control experiments were also performed to ensure that the water vapour was the source of $H_2$ production. Experiments were performed at 28° C. with 20 Torr of $H_2O$ vapour and 280 Torr of Ar in the reaction cell at the start of the experiment, with 20.7 mW cm$^{-2}$ of UV light irradiating the sample disc, equivalent to ~4.5 suns worth of UV intensity (assuming UV<400 nm).

Figure 1:
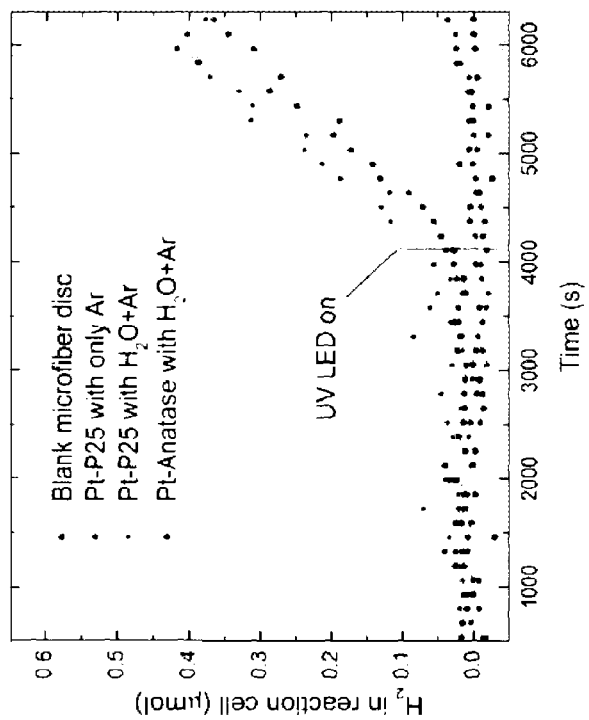
FIG. 1: graph showing $H_2$ gas yield for benchmark Pt—$TiO_a$ photocatalysts and control experiments; the latter of which showed no $H_2$ production.

Selected results of these experiments are presented in FIG. 1. The graph shows that both Pt-P25 and Pt-anatase began to produce $H_2$ gas after the reaction cell was irradiated with UV light. The blank microfiber disc and Pt-P25 without water vapour show no production of $H_2$ after irradiation with UV light, indicating that there is only $H_2$ production when Pt is present on $TiO_2$ or when $Pt—TiO_2$ has access to water vapour. Non-platinised P25 and anatase do not show any measurable levels of $H_2$ production (not shown).

For all $TiO_2$ samples, there is also production of $CO_2$, but no measurable levels of $O_2$ production. This is a consequence of the well-known capacity for $TiO_2$ to photodegrade carbonaceous species in the presence of $O_2$.

Pt-P25 and Pt-anatase have average $H_2$ production rates of 77.1±9.9 and 45.6±12.7 $\mu$mol $hr^{-1}$ $g^{-1}$ $cm^{-2}$, respectively. These results show the well-known effectiveness of Pt co-catalysts in enabling $TiO_2$ to photocatalytically split water. It has been widely accepted that this is due to decreased electron-hole recombination by allowing for greater charge separation via migration of the photo-excited electron to Pt. The unplatinised samples do not produce any notable amounts of $H_2$ as the rate of electron-hole recombination is too high to afford any detectable levels of $H_2$, as $TiO_2$ cannot split water photocatalytically without co-catalysts. The increased performance observed for Pt-P25 compared with Pt-anatase could be due to the mixed polymorphs of anatase, rutile, and amorphous $TiO_2$ present in these nanoparticles, which has been demonstrated to provide a greater degree of charge separation during photo-excitation, as well as possible synergistic effects between anatase and rutile.

Example 3 Effects of Sample Exposure to Vacuum

Figure 2:
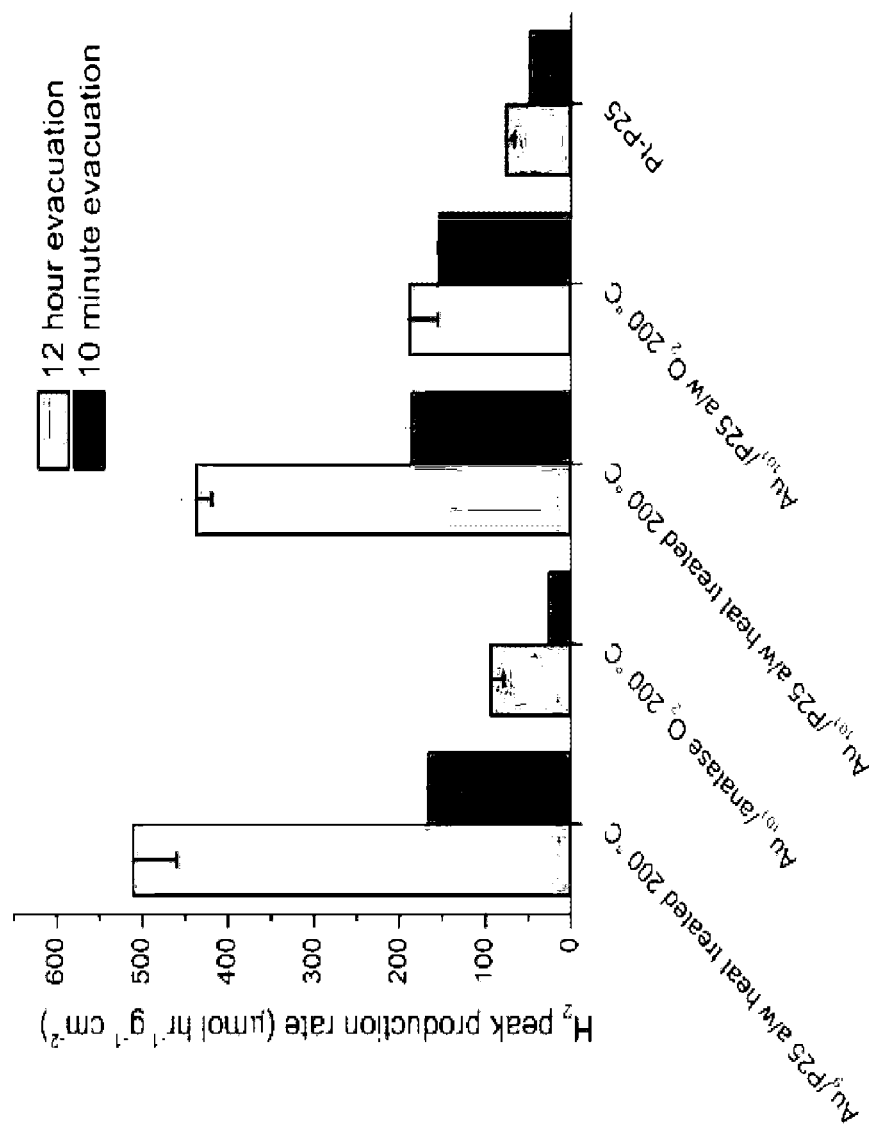
FIG. 2: Bar chart showing a comparison of mean $H_2$ peak production rates for samples that were exposed to vacuum in the reaction cell for 10 minutes, compared with those that were evacuated for 12 hours. Acid-washed supports are denoted with the a/w abbreviation.

Over the course of running control and benchmark experiments, it was discovered that the photocatalytic performance of the catalysts was improved when they were prepared under vacuum for an extended period. Examples of the difference in peak $H_2$ production rates for samples exposed to vacuum for 10 minutes, compared to those exposed to vacuum for 12 hours, are shown in FIG. 2. This effect is most pronounced for the $Au/TiO_2$ samples, such as $Au_9$/acid-washed P25, which has a $H_2$ production rate of 166.9±42.3 $\mu$mol $hr^{-1}$ $g^{-1}$ $cm^{-2}$ for those samples that were exposed to vacuum for 10 minutes, compared with 511.4±51.1 $\mu$mol $hr^{-1}$ $g^{-1}$ $cm^{-2}$ for those that were exposed for 12 hours.

Given that exposing a sample in the reaction cell to vacuum for 12 hours prevented the use of the experiment for other samples, attempts were made to prepare samples under vacuum in a secondary stainless steel cell preparation cell, evacuated overnight, using the same vacuum line as the reaction cell. This secondary cell did not have the features of the primary reaction cell and was only used for the preparation of samples under vacuum. The samples would then be transferred from the secondary cell and into the main reaction cell as rapidly as possible, taking approximately 5 minutes for sample changeover. However, this still resulted in decreased catalytic performance due to the brief exposure to the atmosphere during sample transfer. There must therefore be some effect on the catalysts after exposure to an oxidising environment, even for a short period, compared with those samples that were evacuated within the reaction cell overnight. After this discovery was made apparent for a number of samples, all future samples were prepared for photocatalysis experiments by placing them in the reaction cell and evacuating the cell overnight, then performing experiments without exposing the sample to the atmosphere. Only those samples that have been prepared in this way have been included in the results presented herein. This is similar to most literature studies that undergo rigorous sample preparation procedures, such as extended flushing of reaction cells with Ar or baking samples under UHV for prolonged periods.

Example 4 Effects of Cluster Size

Figure 15C:
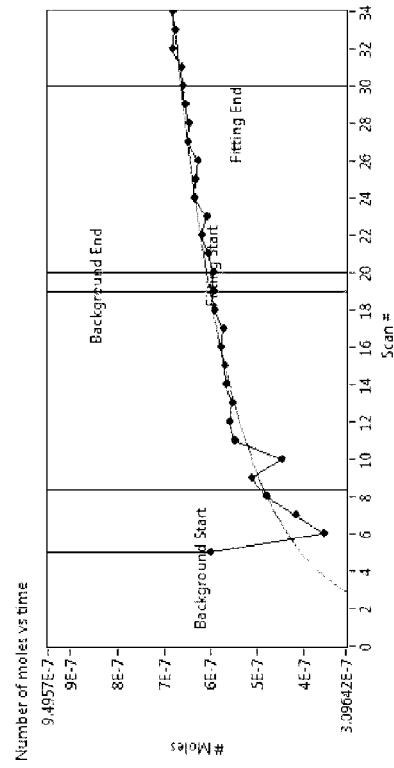
FIG. 15A-H: early experimental data on gold nanoparticles in step (a).
Figure 15D:
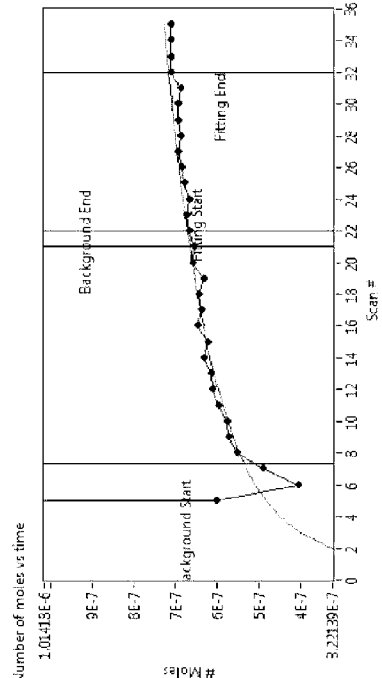
Figure 15A:
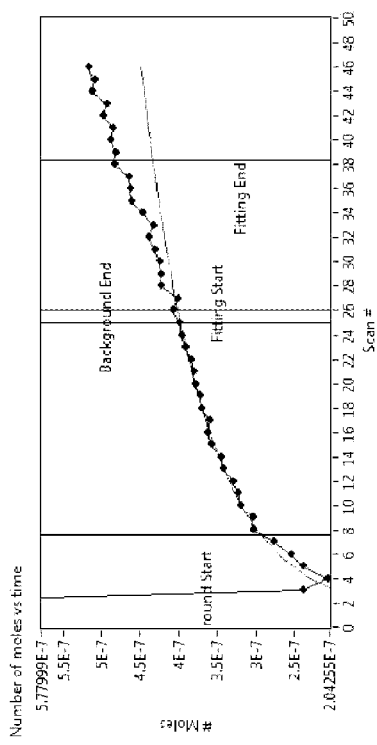
Figure 15B:
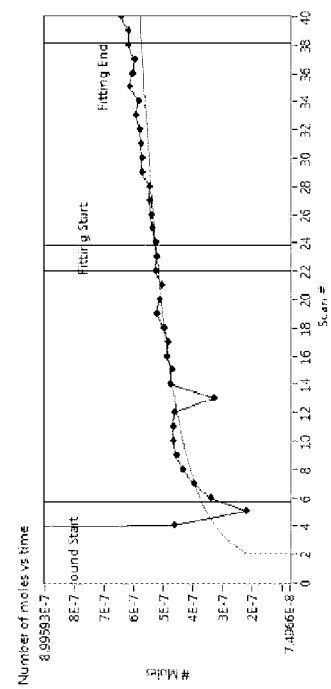
Figure 15E:
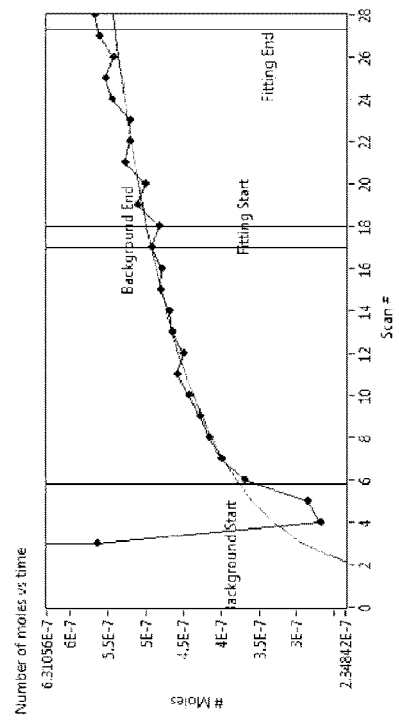
Figure 15G:
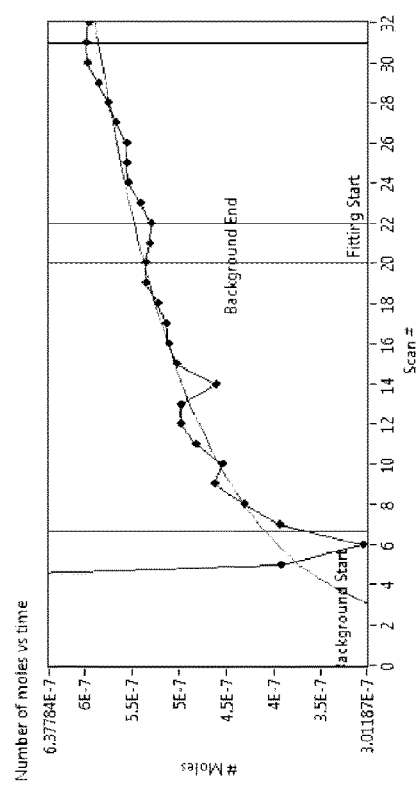
Figure 15F:
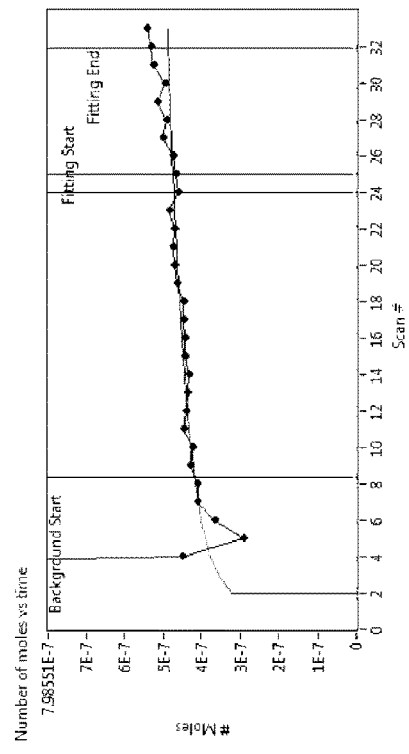
Figure 15H:
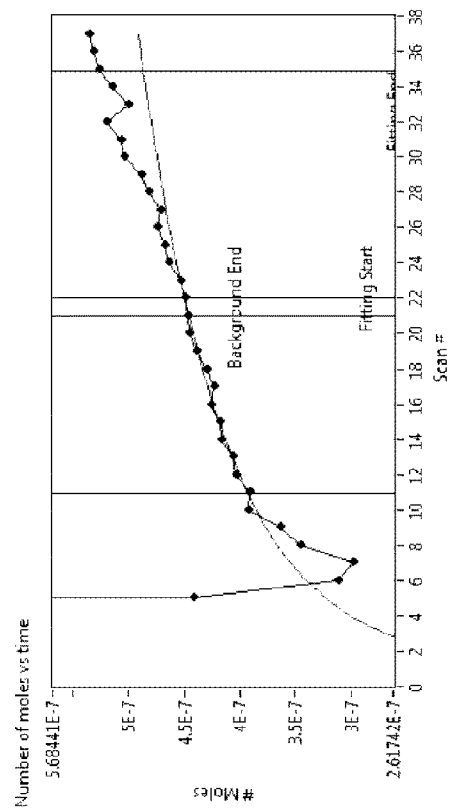

Once the size of the nanoclusters begins to increase over approximately 2 nm, the activity of the photocatalyst appears to decrease. It is thought that as the size of the Au nanocluster increases, the energy levels required for hydrogen production begin to match those of the substrate. This can be seen in FIGS. 15a-h. Various Au nanoparticles samples, with a size of approximately 3-5 nm in size respectively, and which have had various pre-treatments were tested. For the various Au nanoparticles, pre-treatment before hydrogen production includes no pre-treatment (FIG. 15a, f), calcining at 200° C. followed by vacuum (FIG. 15b-d), calcining at 200° C. (FIG. 15e), and calcining 200° C. in the presence of oxygen (FIG. 15g, h). The rate of hydrogen production was usually less than approximately 160 $\mu$mol $hr^{-1}$ $g^{-1}$ $cm^{-2}$.

The $Au_{101}$ nanoclusters used in the following experiments have a size of approximately 1.4 nm and have a much increased hydrogen production yield.

Example 5 Production of $CO_2$ and Consumption of $O_2$

Figure 3:
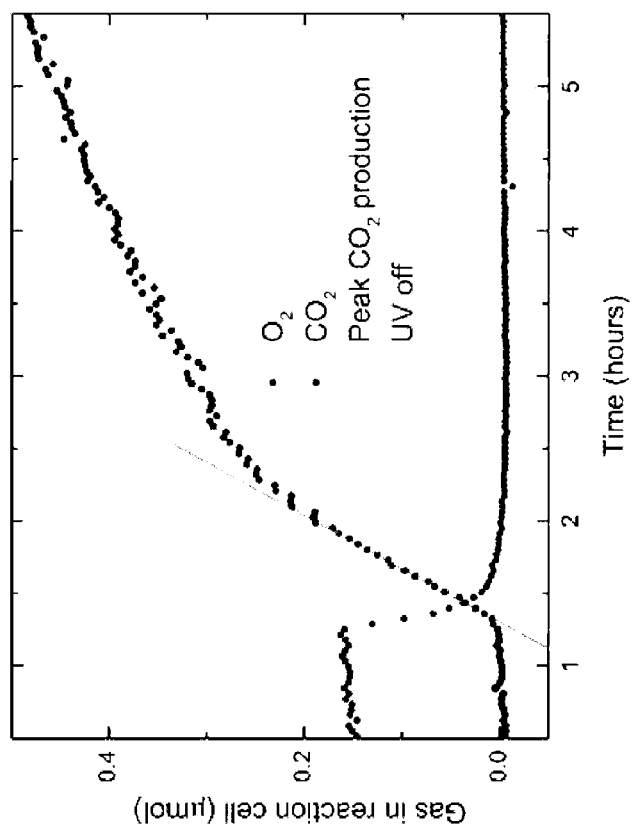
FIG. 3: Graph showing the number of moles of 02 and $CO_2$ in the reaction cell throughout the course of an extended experiment, showing the consumption of $O_2$ and peak $CO_2$ production.

During the water-splitting photocatalysis experiments, the increase in $H_2$ present in the reaction cell upon UV irradiation was accompanied by an increase in $CO_2$, and a decrease in $O_2$, as shown in FIG. 3. It should also be noted that the increased catalytic performance observed between different samples manifest as both an increase in the $H_2$ production rate and an increase in the $CO_2$ production rate.

Studies that deal with the photo-oxidation of organic contaminants present on the $TiO_2$ surface have shown the production of $CO_2$, and this has been suggested to be due to photo-activated oxygen. These studies have shown that even after rigorous steps were taken to dean the $TiO_2$ surface, that even under UHV conditions, there are still carbon contaminants present, which react with oxygen in the system when irradiated with UV light to produce $CO_2$ (vide infra).

One of the most likely sources of carbon in the reaction cell is that of adventitious carbon. This is usually a thin layer of carbonaceous molecules that are found on the surface of any material or vacuum system exposed to the atmosphere. It consists primarily of short chain hydrocarbons and small amounts of single and double bonded, functionalised groups Example 6 Photocatalytic Performance of Au Clusters on $TiO_2$ for Water-Splitting (Step (a))

$Au_8$, $Au_9$, and $Au_{101}$ clusters were supported on P25 and anatase nanoparticles with various treatments as summarised in Table 1.

TABLE 1

A table summarising the different pre- and post-treatments applied to the various supported Au clusters used in photocatalytic experiments.

| Cluster Type | Support | Pre-Treatment | Post-Treatments | Clusters Per Nanoparticle | Approximate Coverage (%) |
|---|---|---|---|---|---|
| $Au_8$ | Anatase | None | Untreated $O_2$ 200° C. $O_2 + H_2$ 200° C. | 25.56 | 5.21 |
| $Au_9$ | Anatase | None | Untreated $O_2$ 200° C. | 22.71 | 4.62 |
|  | P25 | Acid washed | Untreated Heat treated 200° C. $O_2$ 200° C. | 14.31 | 4.13 |
| $Au_{101}$ | Anatase | none | Untreated $O_2$ 200° C. $O_2 + H_2$ 200° C. | 2.02 | 0.81 |
|  | Anatase | Acid washed | Untreated $O_2$ 200° C. $O_2 + H_2$ 200° C. | 2.02 | 0.81 |
|  | P25 | Acid washed | Untreated Heat treated 200° C. $O_2 + H_2$ 200° C. | 1.28 | 0.72 |

TABLE 2

A table sowing a summary of the key trends in ligand loss and agglomeration observed for Au8, Au9, Au11 and Au101 on acid-washed P25 and pure anatase supports under the various post-treatment conditions.

| Treatment | Acid washed P25 Nanoparticle Supported | | | | Pure Anatase Nanoparticle Supported | | |
|---|---|---|---|---|---|---|---|
|  | $Au_8$ | $Au_9$ | $Au_{11}$ | $Au_{101}$ | $Au_8$ | $Au_9$ | $Au_{101}$ |
| Untreated | Virtually Unchanged | | | Small increase in particle size | Partial ligand removal Half of clusters remain intact, while the other half undergo partial agglomeration | | Partial ligand removal Unknown if agglomeration occurs, but likely |
| Washed at 100° C. | Removal of a fraction of clusters from the surface A portion of clusters remain virtually unchanged Some removal of ligands No significant agglomeration Formation of Au—O bonds, to a greater extent for $Au_{11}$ | | | Unknown changes to size Loss of a significant amount of clusters from the surface No Au—O formation | N/A | | |
| Heated at 200° C. | Agglomeration of a portion of clusters while still ligand-protected (these are still smaller than $Au_{101}$) Other portion of clusters lose some ligands and form Au—O and agglomerate to larger particles Of the portion that loses ligands, some clusters may not agglomerate Removal of ligands is less effective for $Au_9$ | | | Further agglomeration of clusters, but still nanoparticulate in nature Removal of some ligands and formation of Au—O bonds | N/A | | |
| Calcined $O_2$ at 200° C. | Increased agglomeration and size distribution | | | | Removal of ligands and agglomeration has progressed further Half of clusters maintain their size | Removal of ligands and agglomeration has progressed further No fraction of clusters maintain their size | Removal of ligands has progressed further Unknown if agglomeration occurs, but likely |
| Calcined $O_2/H_2$ at 200° C. | N/A | | | | Complete ligand removal Agglomeration has progressed further, no evidence of any clusters remaining intact. | | Complete ligand removal Unknown if agglomeration progresses further, but likely. |

Table 2 summarises the key changes to the physical properties of these catalysts due to the various treatments. In general, there is a trend of ligand loss and agglomeration with successively harsher post-treatment conditions. This effect is far more pronounced for clusters supported on pure anatase nanoparticles than on the acid-washed P25 nanoparticles, showing the strong effect of acidic pre-treatment on the interaction between the TiO$_2$ surface and Au clusters. For samples on either support, there is general evidence for two cluster states after post-treatment, with one portion remaining unchanged, while the other undergoes some level of agglomeration.

Example 7 Photocatalytic Performance of the Au$_8$ Cluster

Figure 4:
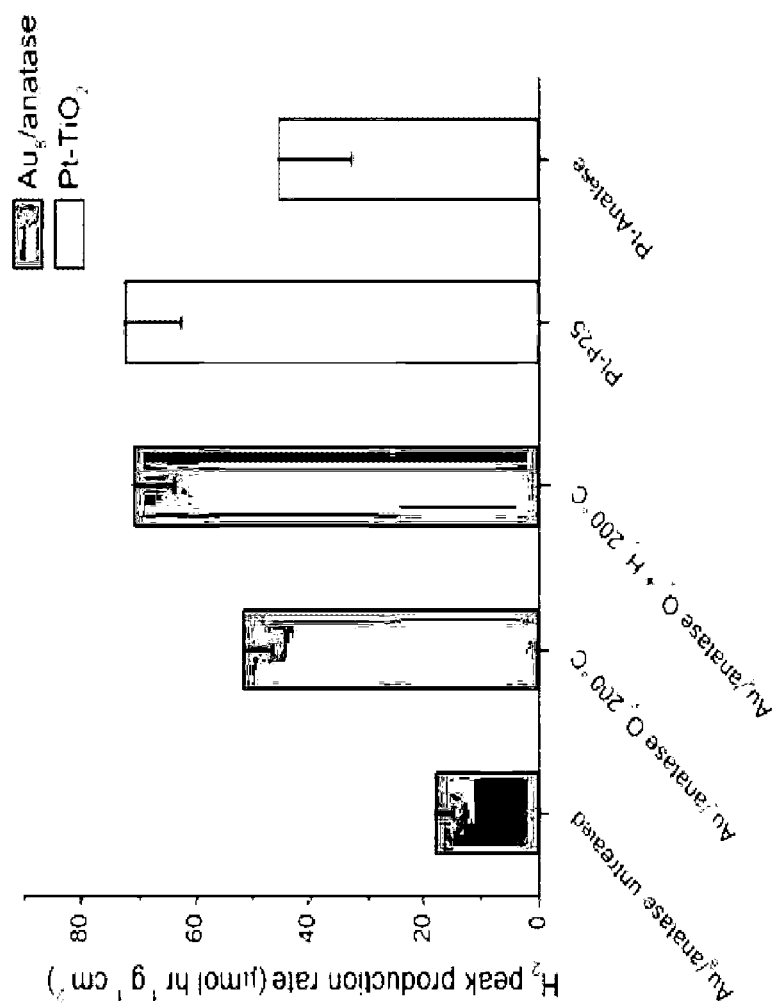
FIG. 4: Bar chart showing average $H_2$ peak production rate for $Au_8$ clusters supported on pure anatase nanoparticles with various treatments.

The peak H$_2$ production rates for Au$_8$/anatase with various treatments are shown in FIG. 4. The Au$_8$/anatase samples have peak H$_2$ production rates of 17.92±3.22, 51.74±5.17, and 71.12±7.11 µmol hr$^{-1}$ g$^{-1}$ cm$^{-2}$ for the untreated, calcined at 200° C. under O$_2$, and calcined at 200° C. under O$_2$+H$_2$ treatments, respectively. There is a clear improvement in H$_2$ gas production as the clusters are treated under successively harsher conditions.

Calcination at 200° C. under O$_2$ for Au$_8$/anatase results in almost complete removal of ligands and agglomeration (See Table 2), while harsher calcination under O$_2$ followed by H$_2$ results in complete removal of ligands. Given this information, it is the exposed Au$_8$ clusters that are more effective catalysts for photocatalytic water-splitting, compared to untreated Au$_8$/anatase, of which there is only partial removal of ligands. However, the loss of ligands may not be the primary cause of increased catalytic activity, given that these calcination treatments bring about agglomerated clusters, which do not maintain their Au$_8$ size. It could therefore be argued that the small size of the Au$_8$ clusters are not beneficial for photocatalytic water-splitting, with larger Au nanoparticles on the anatase surface yielding the best catalytic environment. This is further supported by the deposition of Au$_8$ on anatase without any treatment, which also results in some loss of ligands, and a small fraction of Au$_8$ clusters agglomerating. Given the low, but still present catalytic activity of these untreated samples, this is further evidence that the agglomerated Au$_8$ clusters are the catalytically active sites.

Example 8 Photocatalytic Performance of the Au$_9$ Cluster

Figure 5:
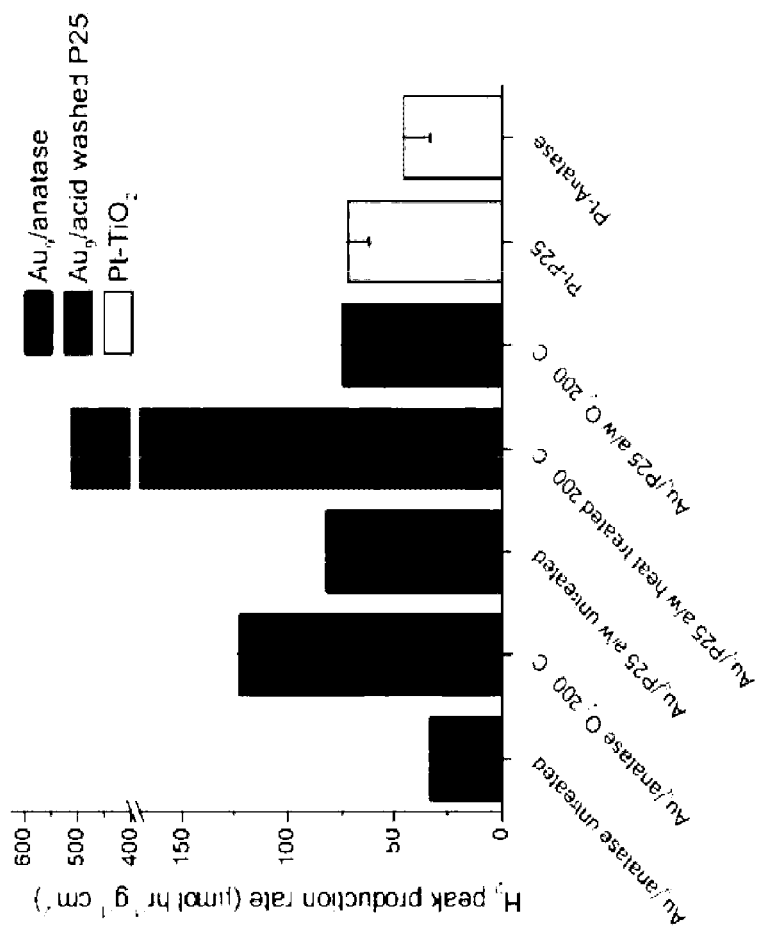
FIG. 5: Bar chart showing average $H_2$ peak production rate for $Au_9$ clusters supported on pure anatase and acid-washed P25 nanoparticles with various treatments.

The average H$_2$ production rates for Au$_9$ supported on anatase and acid-washed P25 nanoparticles with various treatments are shown in FIG. 5. The Au$_9$/anatase samples have H$_2$ production rates of 33.5±3.35 and 112.9±12.3 µmol hr$^{-1}$ g$^{-1}$ cm$^{-2}$ for untreated and calcined under O$_2$ samples, respectively. The acid-washed P25 supported samples yield H$_2$ production rates of 82.7±8.27, 511.4±51.1, and 75.3±7.53 µmol hr$^{-1}$ g$^{-1}$ cm$^{-2}$ for the untreated, heat treated under vacuum, and calcined under O$_2$ samples respectively. There is a clear improvement in productivity for the Au$_9$/anatase clusters after calcination under an O$_2$ atmosphere, whereas for the Au$_9$/acid-washed P25 clusters, there is a large increase in performance after heat-treatment at 200° C. under vacuum, followed by a decrease in performance after further calcination at 200° C. under an Oz atmosphere.

Calcination at 200° C. under O$_2$ for Au$_9$/anatase results in a large degree of ligand removal and agglomeration, with only a fraction of the clusters maintaining their size. Given that this support is not acid-washed, this effect is likely more severe than the same treatment on the acid-washed P25 nanoparticles. This treatment for the anatase-supported Au$_9$ clusters yields a higher production rate than the untreated or calcined under O$_2$ at 200° C. treated, acid-washed P25 supported Au$_9$ clusters, possibly due to the increased size and removal of ligands.

It is therefore interesting that the untreated Au$_9$/acid-washed P25 has a greater performance than untreated Au$_9$/anatase, as the former results in virtually no change in the size or ligand coverage of the Au$_9$ clusters after they are supported. Heat treatment at 200° C. results in agglomeration of a portion of the Au$_9$ clusters while still ligand-protected, while the other portion lose some ligands, forming Au—O bonds, and begin to agglomerate. There is also evidence that of the portion that loses ligands, some may not agglomerate. Further calcination at 200° C. under O$_2$ for Au$_9$/acid-washed P25 results in increased agglomeration according to HRTEM, but there is no XPS data to provide details about ligand removal or bond formation between the cluster and the surface. Without wishing to be limited by theory, it is speculated that the decrease in performance observed for this treatment could imply that there is an ideal size for the Au clusters when supported on acid-washed P25, whereby a small amount of Au$_9$ agglomeration and ligand loss is necessary for ideal performance. Alternatively, it could be the small portion of Au$_9$ clusters that have lost ligands without agglomerating that are the most effective, as these are most likely lost with further calcination at 200° C. under O$_2$. It is difficult to determine if the large differences in performance between the anatase and P25 series is due to the pure vs mixed polymorph nature of the support, or if it is due to the acid-wash pre-treatment, without further characterisation studies.

Example 9 Photocatalytic Performance of the Au$_{101}$ Cluster

Figure 6:
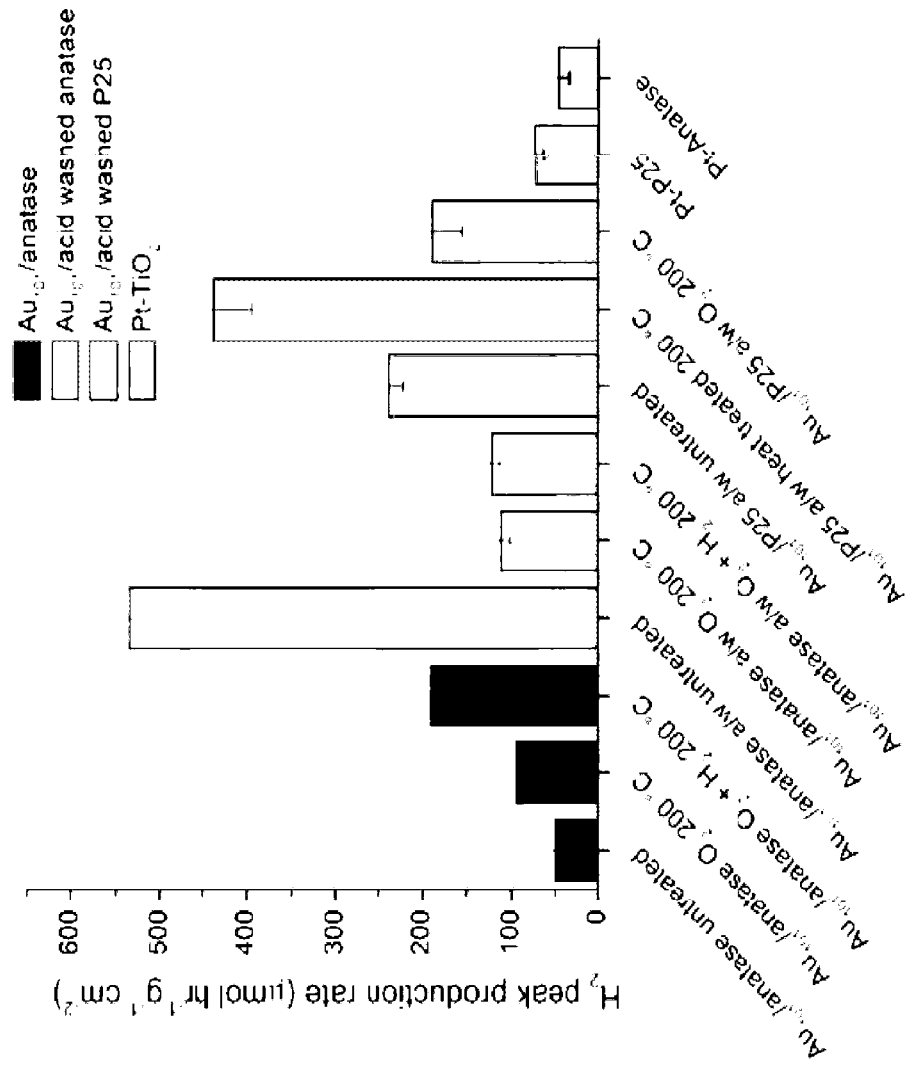
FIG. 6: Bar chart showing average $H_2$ peak production rate for $Au_{101}$ clusters supported on acid-washed P25, treatments. acid-washed anatase, and pure anatase nanoparticles with various treatments

The average H$_2$ production rates for Au$_{101}$ supported on anatase and P25 nanoparticles with various treatments are summarised in FIG. 6. For the Au$_{101}$/untreated anatase series, the production rates are 50.93±13.3, 94.3±15.7, and 190.4±29.6 µmol hr$^{-1}$ g$^{-1}$ cm$^{-2}$ for the untreated, calcined under O$_2$, and calcined under Oz and H$_2$ samples respectively. For the Au$_{101}$/acid-washed anatase series, the production rates are 534.8±53.5, 112.2±11.2, and 122.7±11.2 µmol hr$^{-1}$ g$^{-1}$ cm$^{-2}$ for the untreated, calcined under O$_2$, and calcined under O$_2$ and H$_2$ samples respectively. For the Au$_{101}$/add-washed P25 series, the production rates are 238.3±16.5, 437.5±43.7, and 188.8±34.0 µmol hr$^{-1}$ g$^{-1}$ cm$^{-2}$ for the untreated, heat treated, and calcined under O$_2$ samples respectively.

The trend of increasing H$_2$ production for Au$_{101}$/untreated anatase can be attributed to the increased amount of ligand removal and possible agglomeration under successively harsher calcination conditions. This effect is the same as that discussed previously for both Au$_8$ and Au$_9$, supporting the hypothesis that removal of ligands and certain cluster size improves the catalytic performance of anatase-supported Au clusters.

For the Au$_{101}$/acid-washed P25 series, there is a clear maximum in performance for the heat-treated sample, followed by a decrease with harsher calcination under O$_2$, similar to the trend observed for Au$_9$ previously. Nevertheless, there is no evidence for a bimodal distribution of clusters; instead, all clusters have ligands removed and agglomerate, while forming Au—O bonds to the surface.

Further calcination under $O_2$ results in a decrease in $H_2$ production, with an increase in particle size evidenced by HRTEM. Also of note is that the untreated samples are more effective than those supported on pure anatase, but less effective than those supported on acid-washed anatase. There is evidence to suggest that support of untreated $Au_{101}$ on acid-washed P25 results in virtually no change to the size or ligand coverage of the clusters.

For the $Au_{101}$ clusters supported on acid-washed anatase, the highest $H_2$ production rate is observed for the untreated $Au_{101}$ sample, which is the highest of all samples in this series. The $H_2$ production rate drops significantly after harsher calcination treatments. There is no characterisation data available for this series of clusters, therefore it is unknown if the untreated $Au_{101}$ clusters are maintaining their size after deposition on acid-washed anatase, similar to what occurs for untreated $Au_{101}$ on add-washed P25, or if there is partial removal of ligands as seen for untreated anatase supports. Given that pre-treatment of the $TiO_2$ surface with acid should help to reduce agglomeration, the former seems more likely. If this is the case, then there is a clear performance advantage to keeping the $Au_{101}$ cluster intact on the acid-washed anatase surface. Nonetheless, there is the possibility of a small amount of ligand removal (given the likelihood of this occurring on anatase) comparable to that observed for heat-treated $Au_{101}$ on acid-washed P25, resulting in the similar production rate observed for clusters that maintain size, but have partial ligand removal. This will need to be confirmed with further characterisation experiments in the near future.

Figure 7:
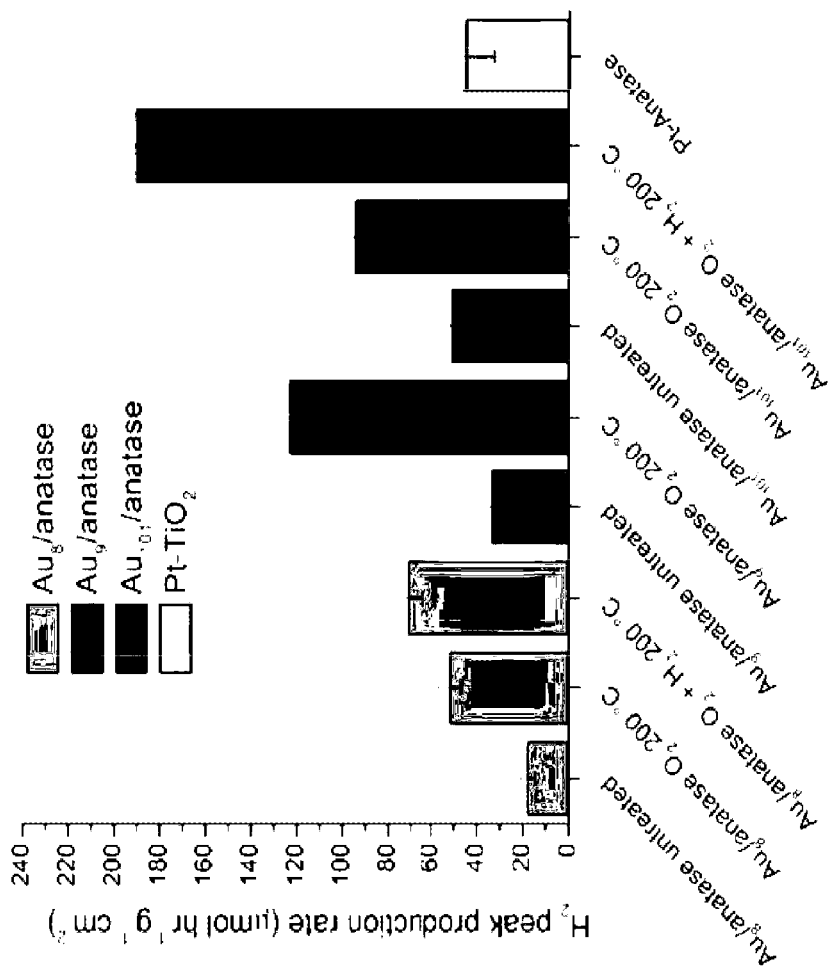
FIG. 7: Bar chart showing a comparison of $H_2$ peak production rate for $Au_8$, $Au_9$, and $Au_{101}$ clusters supported on anatase nanoparticles with various treatments.

Example 10 Overall Comparisons of the Photocatalytic Performance Between Ousters FIG. 7 shows a comparison between $Au_8$, $Au_9$, and $Au_{101}$ clusters supported on anatase nanoparticles. Similar trends are observed for all three clusters as successively harsher post-treatments are applied. When samples are calcined under an $O_2$ atmosphere, their $H_2$ production rate increased compared to their untreated counterparts. When samples are calcined under $O_2$ and $H_2$, a harsher and prolonged calcination, their $H_2$ production rate is increased beyond that of samples calcined under $O_2$ alone. There is no data available for $Au_9$ calcined under $O_2$ and $H_2$, although it can be assumed that it would follow the same trend as the other clusters, given that $Au_9$ calcined under $O_2$ has a production rate within experimental error of the production rate for $Au_{101}$ calcined under $O_2$.

As shown in Table 2, these successively harsher treatments result in increasing ligand removal and agglomeration for all clusters on the anatase surface. It is clear that it is the large, unligated Au particles that have lost their defined size, which are the most effective photocatalysts on the unwashed anatase nanoparticles. Since the overall performance also increases when comparing the set of $Au_8$ to $Au_9$ to $Au_{101}$ samples, this is further evidence that it is the largest Au particles that are the most effective photocatalysts on this support.

Figure 8:
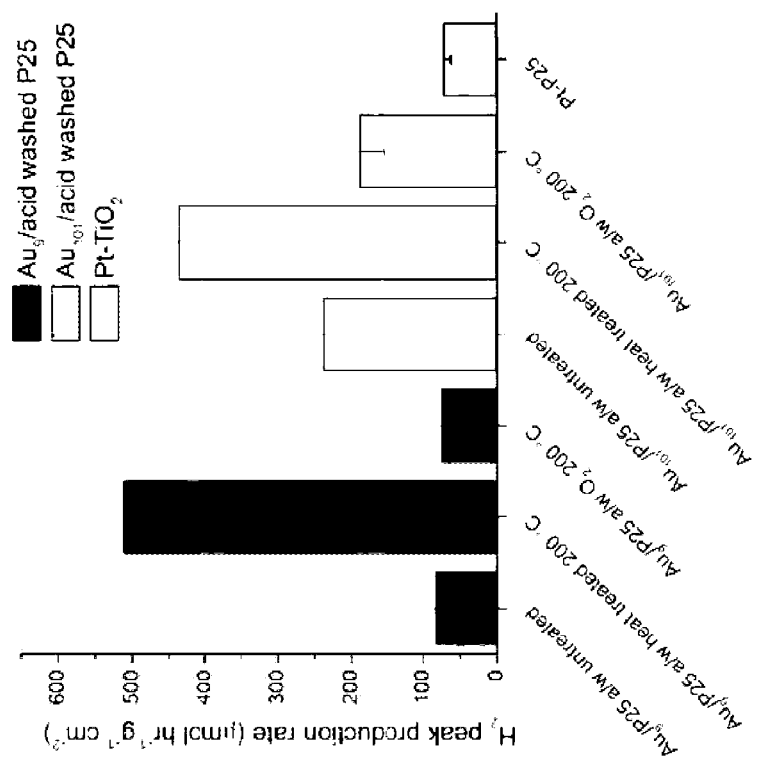
FIG. 8: Bar chart showing a comparison of $H_2$ peak production rate for $Au_8$, $Au_9$, and $Au_{101}$ clusters supported add-washed P25 nanoparticles with various treatments.

FIG. 8 shows the similar trends in $H_2$ production rates for both clusters after treatment, whereby 200° C. heat treatment of the clusters results in a large increase in performance compared to the untreated samples, followed by a decrease in performance for the calcined under $O_2$ samples.

For the untreated samples, it is known that the clusters remain virtually unchanged after being supported on acid-washed P25; therefore, the intact $Au_{101}$ clusters are more effective photocatalysts for water photolysis than $Au_9$. This could be due to their larger particle size, similar to the effect observed for $Au_{101}$ supported on pure anatase nanoparticles.

Comparison between these two clusters also reveals that the untreated $Au_{101}$ clusters do not form any Au—O bonds with the surface; untreated $Au_9$ has a portion of clusters forming Au—O bonds with the surface according to XPS, while untreated $Au_9$ has a portion of clusters forming Au—O bonds.

The production rate of the heat treated samples are within the experimental error of each other, and the size measurement by the HRTEM are also within sampling error of each other (2.4±1.7 vs 3.2±1.7 nm for $Au_9$ and $Au_{101}$, respectively). Therefore, the similar production rate measured for these two clusters on acid-washed P25 with the same treatment could be because the two samples are of similar size after agglomeration, while still being protected by a comparable number of ligands.

The large drop in production rate for $Au_9$ calcined under $O_2$ is surprising given that the size of the nanoparticle is now the same as that of heat-treated $Au_{101}$ according to HRTEM (3.1±2.1 vs 3.2±1.7 nm for $Au_9$ and $Au_{101}$ respectively). There is no XPS data for this treatment, but it could be assumed that the extent of Au—O bond formation has increased, following the increase observed for the heat-treated samples. Since untreated $Au_{101}$ has no Au—O bonds and performs better than untreated $Au_9$ with Au—O bonds, and that $Au_{101}$ calcined under $O_2$ may have an increased amount of Au—O bond formation, it is feasible that high levels of Au—O bond formation is detrimental to the photocatalytic performance. This is further evidenced by $Au_{101}$ calcined under $O_2$ performing worse than the untreated $Au_{101}$ samples.

Figure 9:
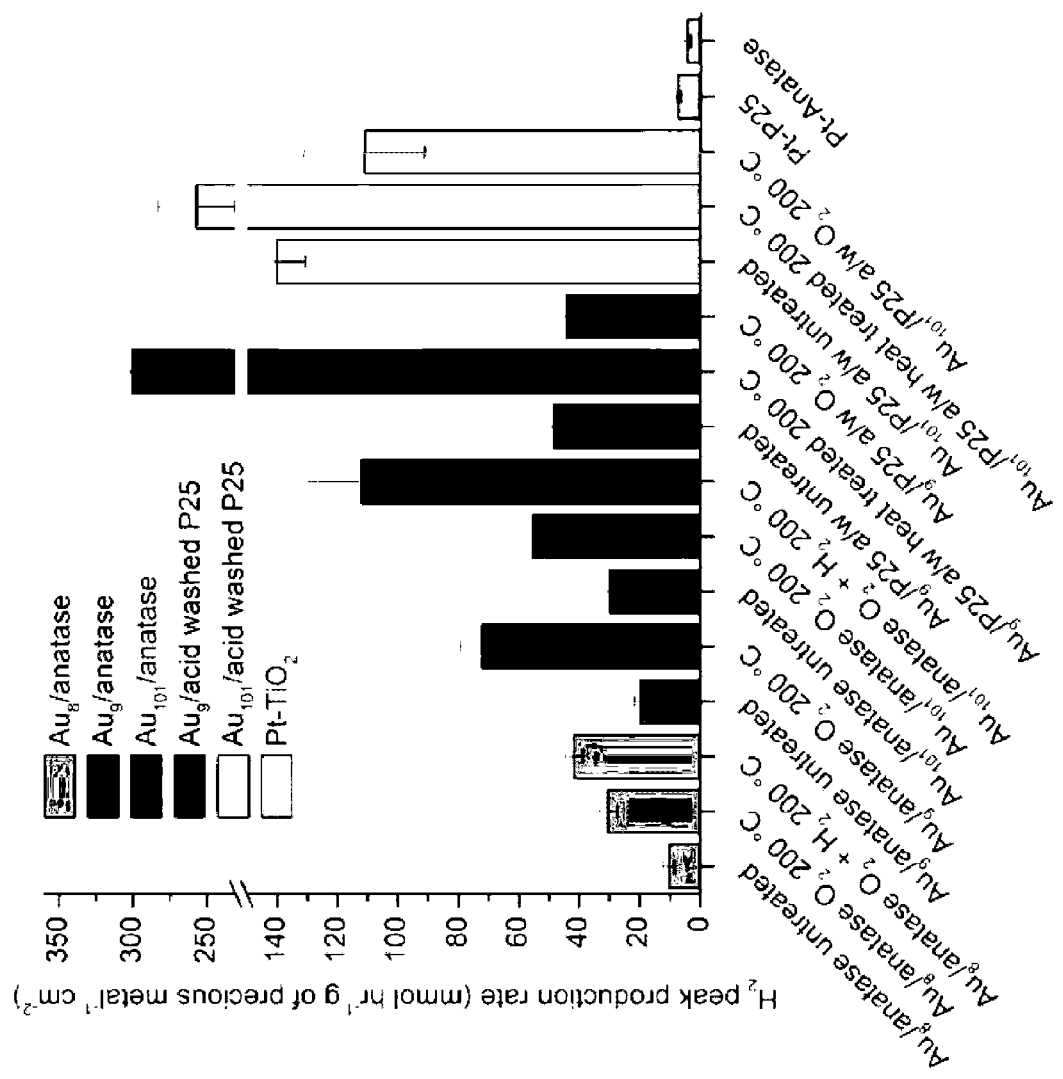
FIG. 9: Bar chart showing a comparison of $H_2$ peak production rate for 0.17% w/w $Au_{101}$, $Au_9$, and $Au_8$ clusters supported on $TiO_2$ against 1.0% w/w Pt-P25 and 1.0% w/w Pt-anatase.

Example 11 Photocotalytic Performance of $Au_8$, $Au_9$, and $Au_{101}$ Compared to Pt—$TiO_2$ Given that $TiO_2$ is cheap and relatively abundant, while both Au and Pt are expensive elements in the current marketplace, it is fair to assume that the major cost of these catalysts would come from the procurement of these two rare elements. Comparison between the production rates for 1.0 wt % Pt-P25 and 1.0% Pt-anatase to that of the 0.17 wt % Au supported on P25 or anatase nanoparticles can be made by normalising for the amount of precious metal present in the catalyst instead of by the total mass of the catalyst; these $H_2$ production rates normalised by precious metal mass are shown in FIG. 9.

This comparison shows the increased efficacy of Au/$TiO_2$ compared to typical Pt—$TiO_2$ photocatalysts. For the anatase-supported series, $Au_{101}$ calcined under $O_2$ and $H_2$ is ~20 times more effective than Pt-anatase for the same amount of precious metal present in the catalyst, while for the P25 series, heat-treated $Au_9$ is ~66 times more effective than Pt-P25 for the same amount of precious metal present in the catalyst. Even the least effective Au catalyst in the series, untreated $Au_8$ on pure anatase, is more effective than both Pt-P25 and Pt-anatase when compared using this normalisation scheme.

Conclusions from Examples 1 to 11

Benchmark photocatalytic water-splitting experiments were undertaken using Pt-P25 and Pt-anatase nanoparticles to ensure the newly designed experimental apparatus was performing adequately. During these studies, it was discovered that there Is a decrease in the photocatalytic performance of samples when repeating experiments using the same catalyst material. Further preliminary studies of Au/TiO$_2$ found a similar effect of performance degradation. This degradation in the performance of samples was accompanied by a colour change in the samples. The degradation and colour change of samples was attributed to accumulation of carbon deposits during the oxidation of organic compounds, and may be related to the known photo-induced agglomeration effects of ambient light on the Au$_9$ and Au$_{101}$ clusters evidenced by XANES and HRTEM data. Improved performance was also observed for all samples prepared in the reaction cell with 12 hours of exposure to vacuum, compared to relatively short vacuum exposure times of 10 minutes.

The production of H$_2$ from photocatalytic water-splitting experiments was accompanied by the production of CO$_2$ and consumption of O$_2$. The CO$_2$ by-product arises from the well-known capacity for TiO$_2$ to photo-oxidise organic contaminants, and consumes the stoichiometrically evolved Oz from the water-splitting reaction throughout the experiment. The source of carbon in the reaction cell is most likely from unavoidable adventitious carbon that is present in all vacuum systems and samples exposed to atmosphere, in addition to the possible contribution from oil back-streaming from the rotary pump. Various carbon based sealant material used in the reaction cell and adsorbed CO that is difficult to evacuate during sample preparation may also contribute to the source of carbon.

O$_2$ present in the reaction cell at the beginning of the experiment due to low vacuum is likely rapidly consumed by quenching defect states within the TiO$_2$ nanoparticles and by photo-adsorption of O$_2$ to the TiO$_2$ surface over the initial hour of experiments. This initial 02 presence could also include O$_2$ molecules adsorbed to the TiO$_2$ surface at ambient temperature, or those adsorbed to the walls of the reaction cell. The formation of surface O$_2^-$ and O$_3^-$ species during this period by molecular O$_2$ likely behaves as electron traps or hole scavengers after photo-excitation, increasing electron-hole separation, which could explain the decrease in both H$_2$ and CO$_2$ production after the excess O$_2$ in the reaction cell is consumed.

Example 12 Ru$_3$ Nanoclusters on Titania

Ru clusters have interesting properties when it comes to catalysis and these are mostly unexplored. The materials explored in this example are ligand stabilised clusters on a titania support. All the experiments were conducted at 2 bar with a 4:1 ratio of H$_2$ to CO$_2$. All Ru clusters were loaded at 0.17% on titania.

For Ru$_3$ a series of experiments were performed testing different Ha calcination temperatures. A reactor was filled to 1.5 bar with H$_2$, and heated to the target temperature at a rate of 10° C. per min. A series of different reaction temperatures were tested, a series of different masses on a substrate were tested and finally a series of varying evacuation techniques.

Figure 10:
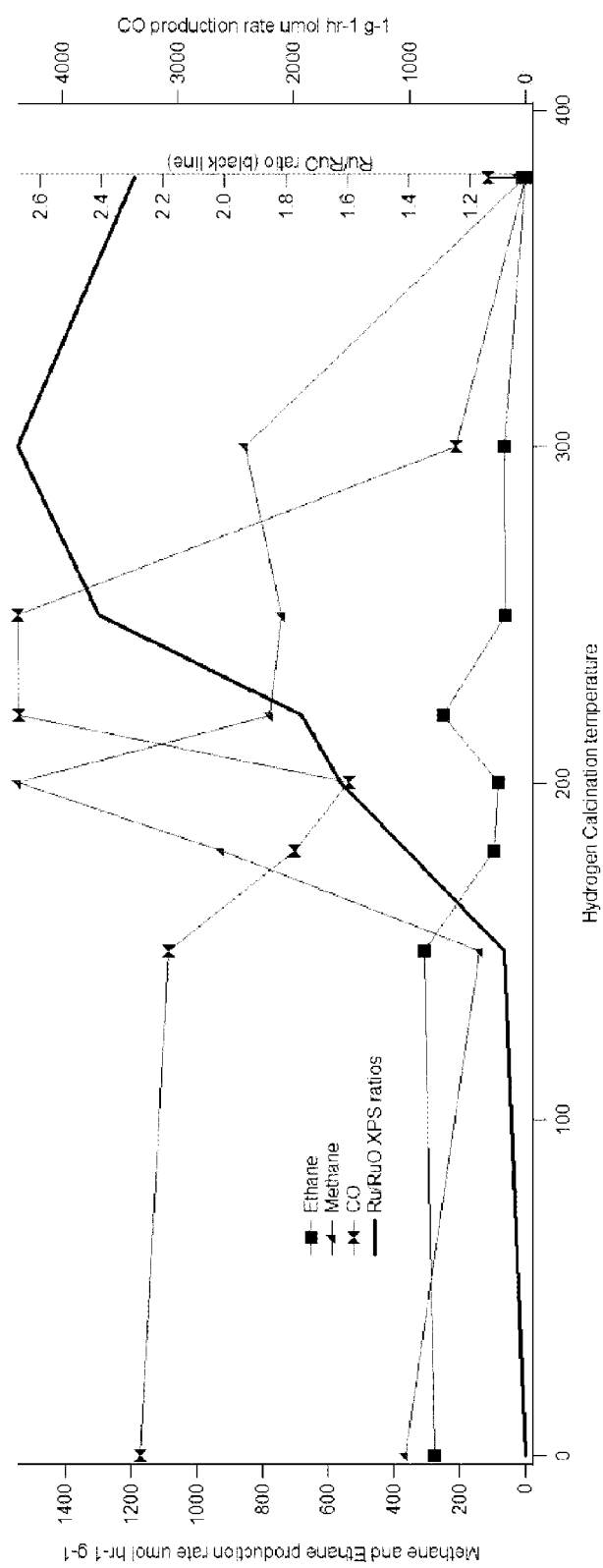
FIG. 10: Graph showing hydrocarbon production following photocatalyst treatment at varying calcination temperature. The reaction temperature was set at 220° C. for each of the runs.

FIG. 10 shows the production rates at varying calcination temperatures for CO, methane and ethane (note the axis is on the right for CO). For each of these samples XPS data was also gathered, and saw partial oxidation at higher calcination temperatures. The species of Ru are yet to be clearly identified but it is known from XPS that a RuO forms. Initial tests were carried out over several hours with Ru nanoclusters on titania. The Sabatier mix used was 3:1 ratio of H$_2$ to CO$_2$ with the aim to produce methanol.

Figure 11:
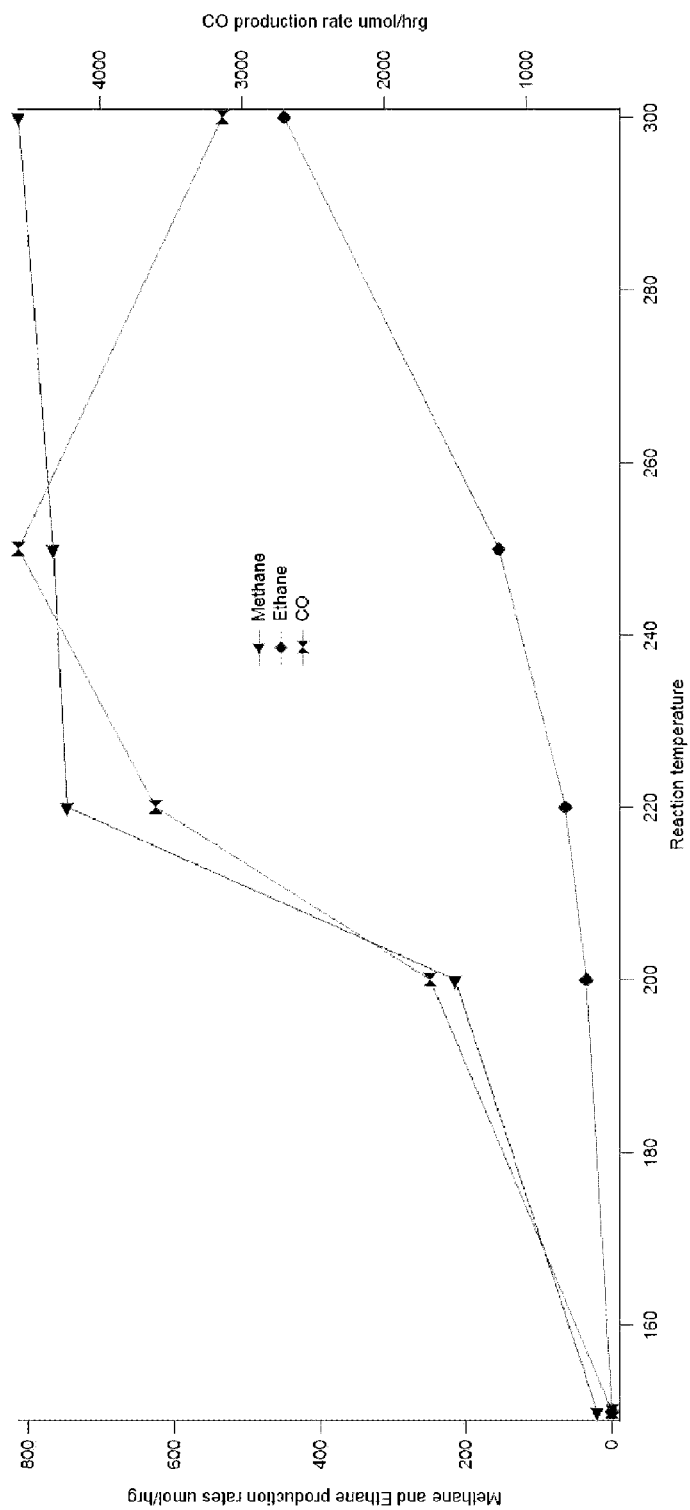
FIG. 11: early experimental data on ruthenium nanoclusters ($Ru_3$) in step (b).

After identifying a consistent calcination temperature, a series of samples at different reaction temperatures were explored. Surprisingly relatively low temperatures are required, contrary to literature where values of 300° C. and above are reported. FIG. 11 shows there is a clear saturation after 220° C., ideal temperature being 250° C.

Example 13 Ru$_4$ Nanoclusters on Titania

At a calcination temperature of 200° C. and a reaction temperature of 250° C. the gases produced are 379 µmolh$^{-1}$ g$^{-1}$ of methane, 4649 µmolh$^{-1}$ g$^{-1}$ of CO and 149 µmolh$^{-1}$ g$^{-1}$ of ethane.

Ruthenium nanoparticles at a 3% loading produced in the range of 2000-3000 µmolh$^{-1}$ g$^{-1}$ of methane, but had 20 times more Ru than the cluster samples. Production rate normalised to Ru mass shows that Ru clusters out-perform the ruthenium nanoparticles by almost 4 times as much.

Figure 14:
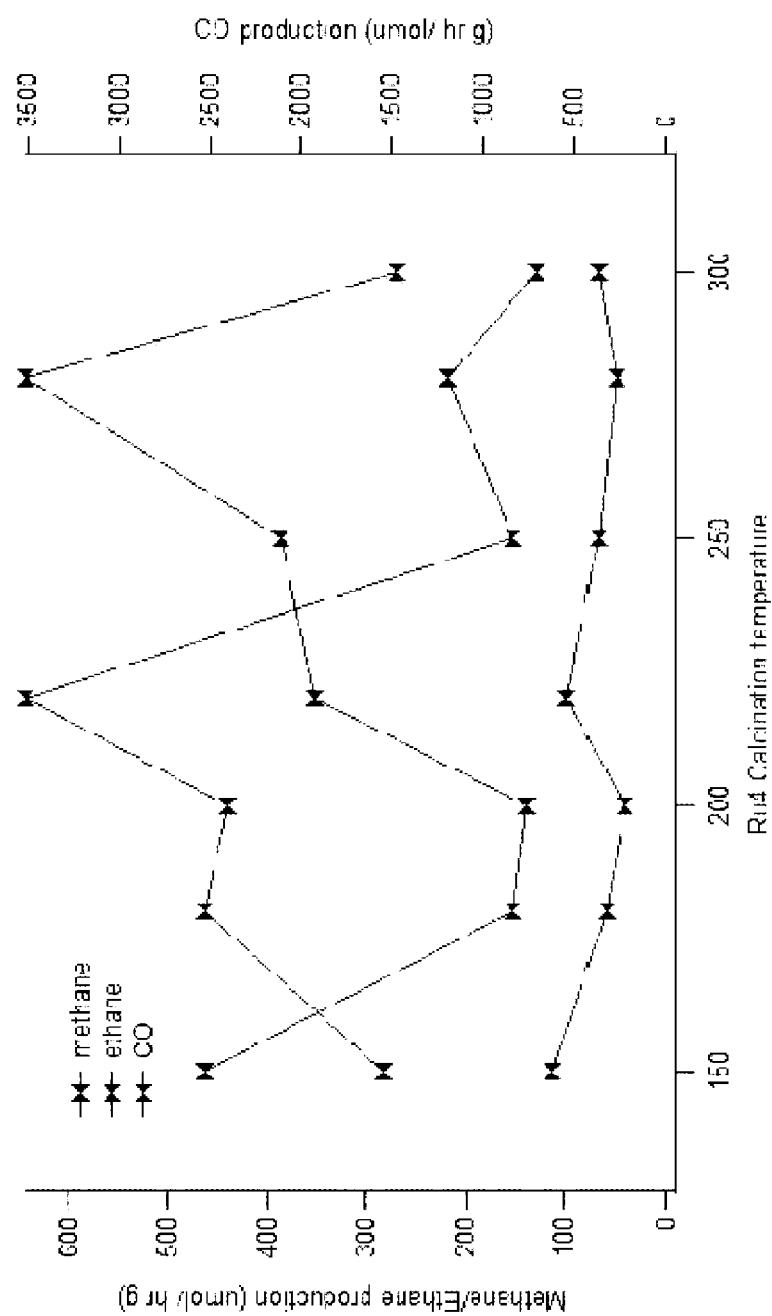
FIG. 14: early experimental data on ruthenium nanoclusters in step (b).

To compare Ru$_4$ with Ru$_3$ nanoclusters, the same series of hydrogen calcinations was completed at the same temperature. These are plotted in FIG. 14. CO production was similar for both, but Ru$_3$ had a general better production rate for methane and ethane.

Example 14 the Effect of the Thickness of the Photocotalyst in Step (b)

Figure 12:
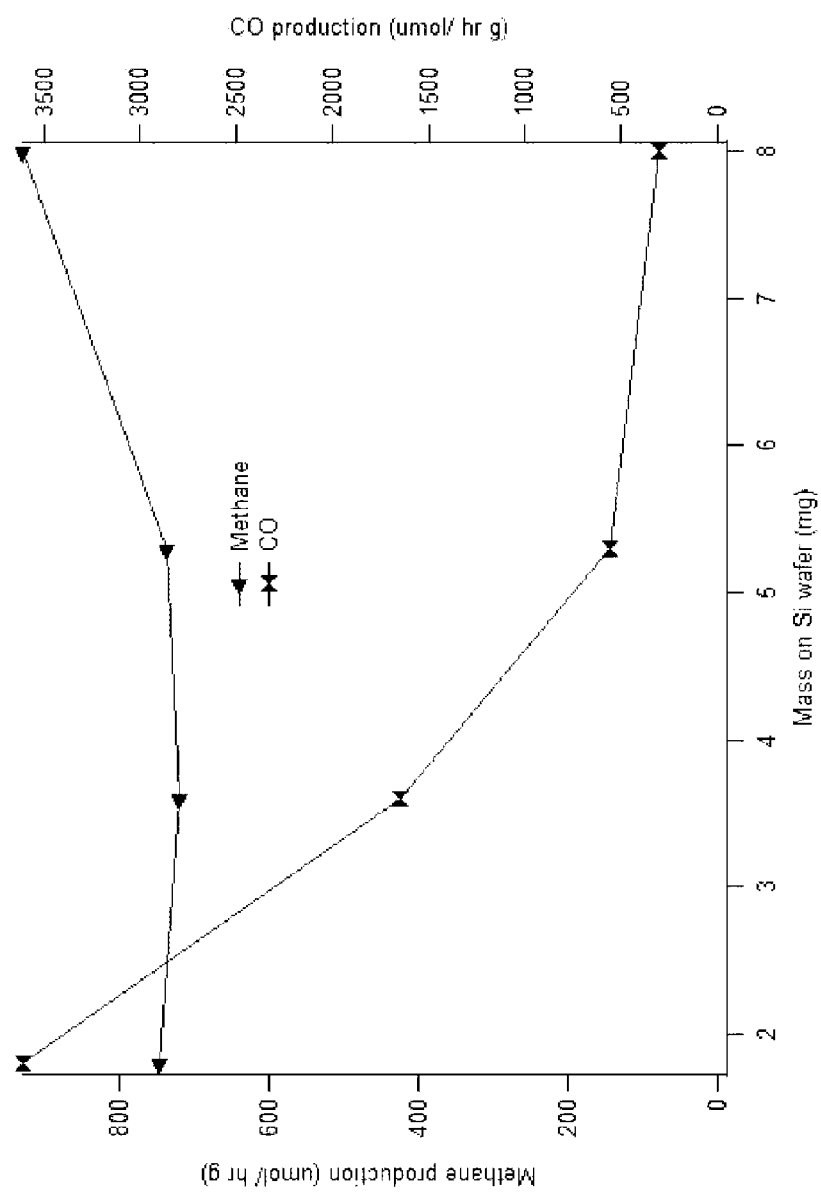
FIG. 12: early experimental data on ruthenium nanoclusters ($Ru_3$) in step (b).

Experiments were performed in order to determine the effect of the thickness of the deposited photocatalyst on a silicon wafer substrate and whether it had an effect on the hydrocarbon gas production rates. For this experiment the weight of catalyst on the wafer was determined. FIG. 12 shows that lower loadings on the Si wafer produced more CO, decreasing with weight. Whilst methane was pretty stable throughout, yet still increasing slightly as the mass increased.

Figure 13:
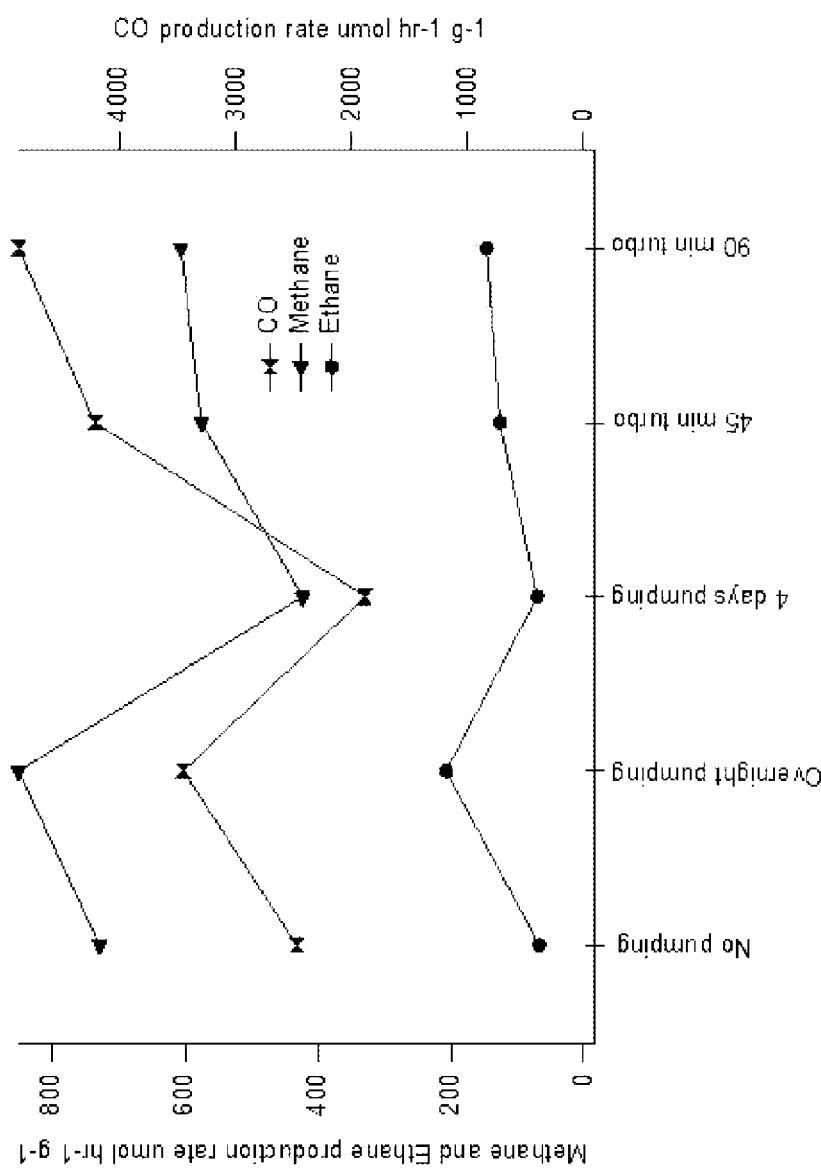
FIG. 13: early experimental data on ruthenium nanoclusters ($Ru_3$) in step (b).

Prior to this, all samples were left overnight in the reactor pumped overnight using a rotary vane pump; reaching pressures of approx 1.102 mbar. A series of different conditions were tested, as shown in FIG. 13. After each evacuation, the samples were calcined at 200° C. in H$_2$ at 1 bar. The reaction temperature was 250° C.

Example 15 Photocatalytic Studies of AuRu$_3$ Deposited Upon Anatase TiO$_2$

The Ru$_3$(µ-AuPPh$_3$)(µ-Cl)(CO)$_{10}$ cluster was deposited upon anatase TiO$_2$, (hereinafter referred to as "AuRu$_3$—TiO$_2$") and was evaluated for photocatalytic solar fuel production in the gas-phase, using a heterogeneous batch reactor apparatus. H$_2$ and methane were detected as the major products of these reactions, with longer-chain hydrocarbons up to C$_4$ species observed as minor products under certain conditions.

Example 15.1 Synthesis of Ru$_3$AuPPh(µ-Cl)(CO)$_{10}$

The Ru$_3$AuPPh$_3$(µ-Cl)(CO)$_{10}$ was synthesised as follows along the lines of the technique described in the paper entitled Synthesis and Structural Characterization of a New Ruthenium-Gold Cluster Complex: Ru$_3$AuPPh$_3$(µ-Cl)(CO)$_{10}$, Inorganic Chemistry, Vol. 23, No. 5, (1984). In typical synthesis, 310 mg of Ru$_3$(CO)$_{12}$ and 240 mg of AuPPh$_3$Cl were dissolved in 50 mL of dry dichloromethane. The solution was stirred and refluxed (at 50° C.) under N$_2$ atmosphere overnight. After the reaction mixture was cooled to room temperature, silica gel 60 was added. The solvent was removed under vacuum for about an hour. The reaction mixture was chromatographed on silica gel 60. Elution with toluene-petroleum ether (1-1) afforded yellow band of Ru$_3$ (CO)$_{12}$. Further elution with pure toluene afforded violet band of Ru$_3$AuPPh$_3$(μ-Cl)(CO)$_{10}$. After solvent removal in vacuo, dichloromethane-hexane (1-5) was added. The solvent was removed under reduced pressure using rotary evaporator to obtain the crystals of the violet solution.

Drying Anotase

A 12 g (12.0749 g) of anatase was dried in vacuo at 200° C. for 5 hours with stirring. After cooling to room temperature, dry anatase was kept in desiccator overnight. A 1.9% weight loss was found according to moisture content.

Preparation of Ru$_3$AuPPh$_3$(μ-Cl)(CO)$_{10}$ Stock Solution

A 300 mg (302.13 mg) of Ru$_3$AuPPh$_3$(μ-Cl)(CO)$_{10}$ crystals was dissolved in small amount of dichloromethane. The solution was transferred into 25-mL volumetric flask following by making volume up to 25 mL by adding dichloromethane to obtain Ru$_3$AuPPh$_3$Cl(CO)$_{10}$ stock solution.

Deposition Ru$_3$AuPPh$_3$(μ-Cl)(CO)$_{10}$ on Anatase

X grams of dry anatase (see Table below) was suspended in 20 mL of dichloromethane in a Schlenk tube. After vigorously stirring (750 rpm) under N$_2$ for 30 min, a Y μL of Ru$_3$AuPPh$_3$Cl(CO)$_{10}$ stock solution was injected into the Schlenk tube. The solution was stirred (750 rpm) at room temperature under N$_2$ for 90 min. The solvent was carefully removed under vacuum for around an hour to obtain Ru$_3$AuPPh$_3$(μ-Cl)(CO)$_{10}$ deposited on anatase. The final catalyst was sonicated and then transferred into a sealed vial.

| % metal loading | X, Anatase (g) | Y, Ru$_3$AuPPh$_3$Cl(CO)$_{10}$ stock solution (μL) |
| --- | --- | --- |
| 0.08 | 1.1990 (1.19978) | 172 |
| 0.17 | 1.1980 (1.19843) | 366 |
| 0.35 | 1.1958 (1.19522) | 754 |
| 0.50 | 1.1940 (1.19435) | 1078 |
| 0.75 | 1.1910 (1.19137) | 1616 |
| 1.00 | 1.1880 (1.18806) | 2155 |
| 1.50 | 1.1820 (1.18252) | 3233 |
| 2.00 | 1.1760 (1.17650) | 4311 |
| 5.00 | 1.1400 (1.14039) | 10776 |

Example 15.2 Photocatalytic Benchmarks and Comparisons

AuRu$_3$/TiO$_2$, Pt/TiO$_2$ & Bare TiO$_2$

To assess the relative photocatalytic activity of AuRu$_3$/TiO$_2$ towards CO$_2$ reduction, two other materials were tested as benchmarks. Bare anatase TiO$_2$ nanoparticles (Sigma-Aldrich) were tested as-purchased, as well as 1 wt % Pt nanoparticles deposited upon P25 TiO$_2$. Preliminary testing indicated that pre-treatment and reaction temperatures of 200° C. and a P$_{CO2}$:P$_{H2O}$ ratio of 3 were optimal for solar fuel production, and so these conditions were used for testing all samples. These will hereafter be referred to as "standard conditions".

H$_2$ and methane were detected as major products, as well as trace amounts of C$_2$-C$_3$ alkane and alkene species. To ensure that the source of these products was indeed the reagent gases and not other carbonaceous contaminants, control reactions were conducted (i) without catalyst, in the presence of UV irradiation and reagent gases; (ii) in the absence of UV Irradiation, with catalyst and reagent gases, and (iii) with catalyst under UV irradiation, but with argon buffer gas used in place of the reaction mixture. The former two tests yielded negligible amounts of the products of interest here, however the third blank test gave off trace levels of C$_1$-C$_3$ hydrocarbons. Further investigation showed that these residual hydrocarbon levels scaled linearly with the mass of catalyst used, and is likely due to the photo-induced breakdown of surface-adsorbed advantageous hydrocarbons or ligands. This background hydrocarbon production was normalized to total catalyst mass, and subtracted from all subsequent photocatalytic tests.

Figure 16A:
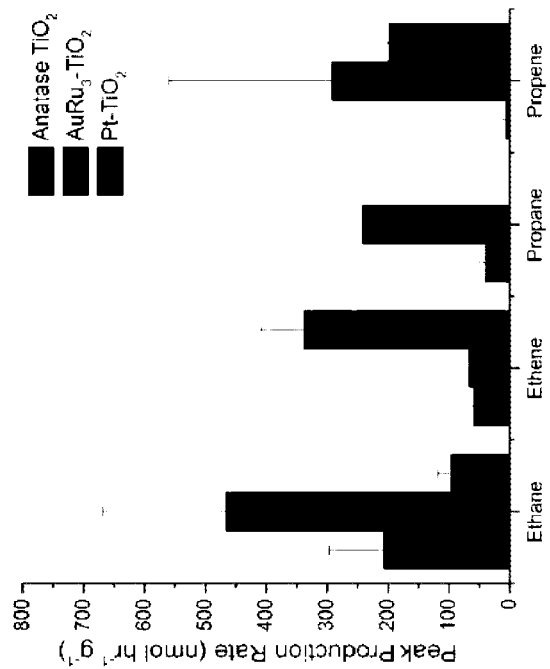
FIG. 16A: Peak production rates of (left) $CH_4$ and (right) $H_2$ by various photocatalysts tested. Average production rates are shown from three independent tests, with error bars representing the standard error in the mean of these. Standard reaction conditions were used for all tests: pre-treatment under vacuum at 200° C., reaction at 200° C., $P_{CO2}$: $P_{H2O}$=3.
Figure 16B:
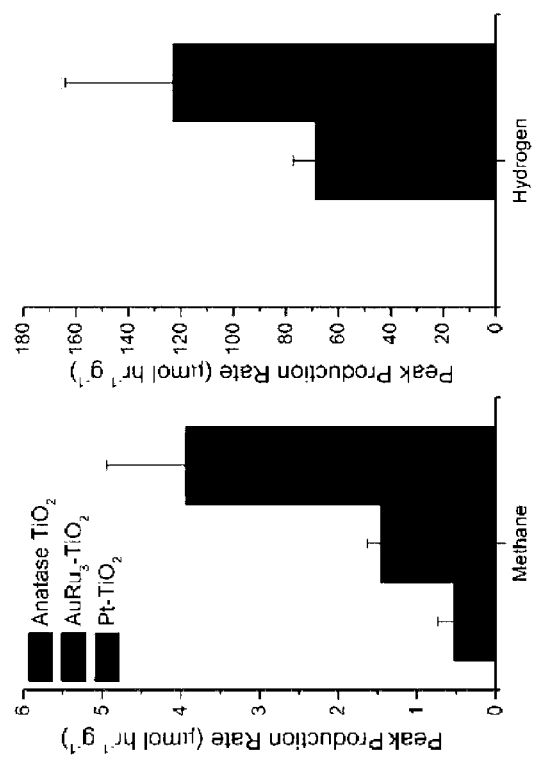
FIG. 16B: Peak production rates of longer-chain hydrocarbon products by various photocatalysts tested. Standard reaction conditions were used for all tests.

Photocatalytic production rates of methane and hydrogen by anatase TiO$_2$, AuRu$_3$/TiO$_2$ and Pt/TIO$_2$ are shown in FIG. 16A. Production rates of minor, longer-chain hydrocarbon products are then shown in FIG. 16B. Deposition of the AuRu$_3$ duster improves the turnover of both major and minor hydrocarbon products relative to bare anatase, with methane production increasing by ~3× and ethane by a factor of two. In the case of the minor hydrocarbon products, the large uncertainties make Interpretation of this data difficult. These errors are predominantly due to the extremely low levels of these products generated (~10-100 ppb), giving poor signal-to-noise ratios in the GC-FID. However, it can be said with confidence that generation of C$_3$ products propane and propene is greater for the AuRu$_3$-deposited sample than the bare titania, as these production rates do not agree even under these large experimental errors. Additionally, negligible H$_2$ production is observed over the bare anatase substrate, whereas the AuRu$_3$/TiO$_2$ system generates 68.5 μmol hr$^{-1}$ g$^{-1}$.

When comparing the activities of AuRu$_3$/TiO$_2$ with Pt/TiO$_2$, the latter shows higher production rates for both methane and hydrogen. This is unsurprising considering the greater content of co-catalyst on platinized sample than on the cluster-deposited sample (vide infra). However, greater amounts of saturated, longer-chain hydrocarbon products ethane and propane are generated by AuRu$_3$/TiO$_2$ than Pt/TiO$_2$. The same cannot be said for unsaturated products; Pt—TiO$_2$ generates more ethene than AuRu$_3$/TiO$_2$, and the levels of propene generated by these two catalysts agree under experimental error. Evidently, Pt/TiO$_2$ has a much higher selectivity for the formation of unsaturated hydrocarbon products than AuRu$_3$/TiO$_2$.

Figure 17A:
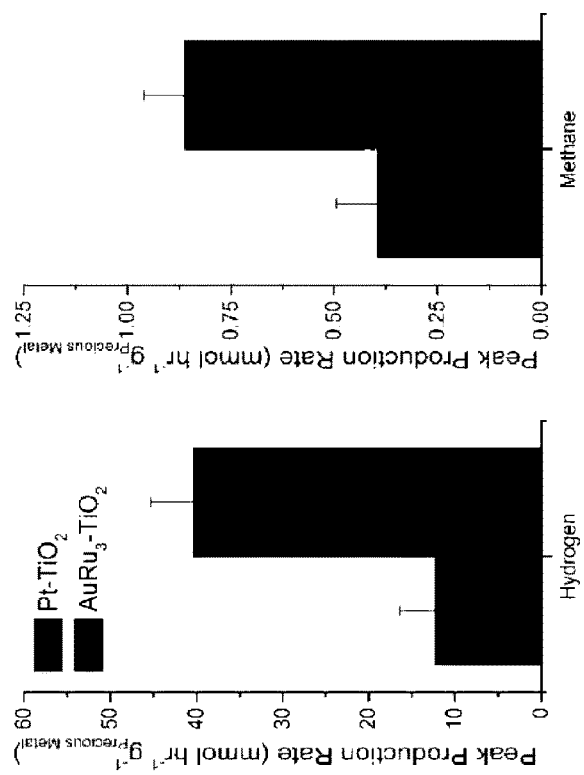
FIG. 17A Peak production rates of (left) $H_2$ and (right) $CH_4$ products by various photocatalysts tested, normalised to total precious metal content of co-catalysts.
Figure 17B:
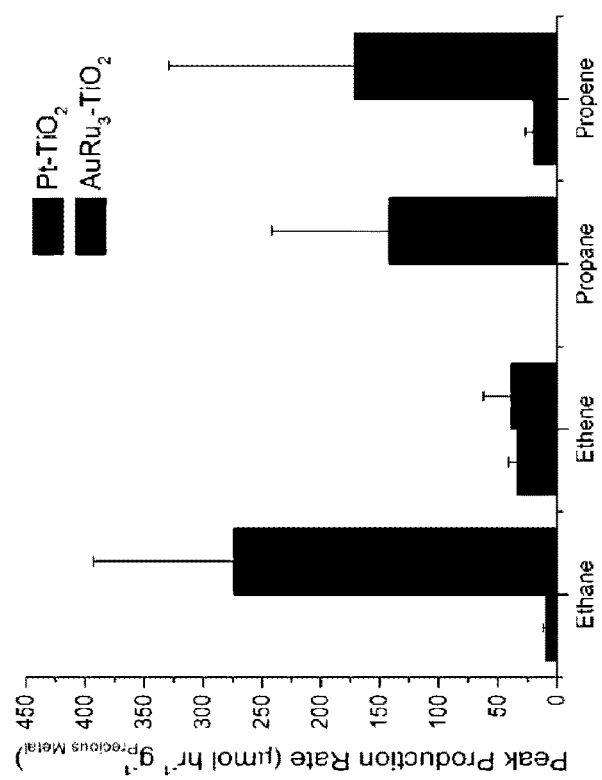
FIG. 17B: Peak production rates of longer-chain hydrocarbon products by various photocatalysts tested, normalised to total precious metal content of co-catalysts.

To account for the different loadings of co-catalyst upon AuRu$_3$—TiO$_2$ and Pt—TiO$_2$, FIGS. 17A and 17B show the same production rates discussed above, but instead normalized to the total precious metal content (Pt or Au/Ru) deposited upon the TiO$_2$ nanoparticles. As can clearly be seen when compensating for total co-catalyst content, the cluster-based AuRu$_3$/TiO$_2$ out-performs Pt/TiO$_2$ in the generation of all products detected here. As platinum nanoparticles can be highly-active co-catalysts for CO$_2$ photo-reduction this is extremely promising for potentially further improving the efficiency of these reactions by use of sub-nanometer clusters instead of nanoparticles. However, as the cluster and nanoparticle co-catalysts compared here have entirely different elemental compositions, it must be acknowledged that the improved activity of AuRu$_3$/TiO$_2$ may be due to selection of a more appropriate metal for this reaction as well as (or instead of) the benefits of sub-nanometer co-catalysts over nanoparticulate species.

Figure 18B:
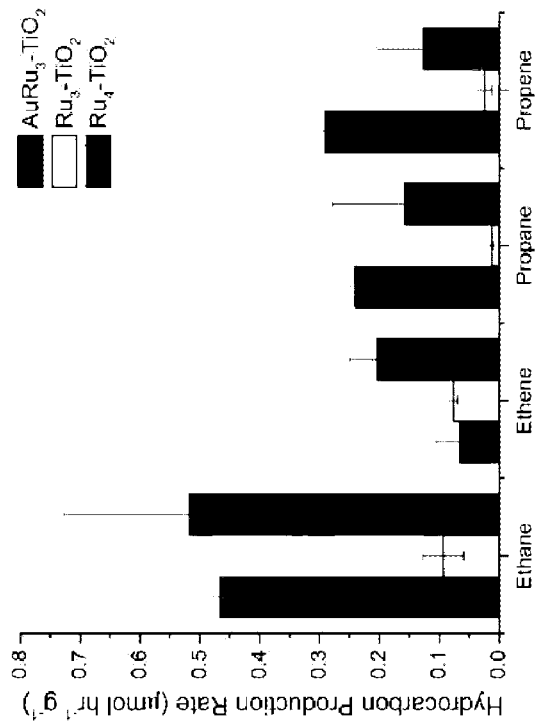
FIG. 18B: Peak production rates of longer-chain hydrocarbon products by all cluster-deposited titania materials tested here.
Figure 18A:
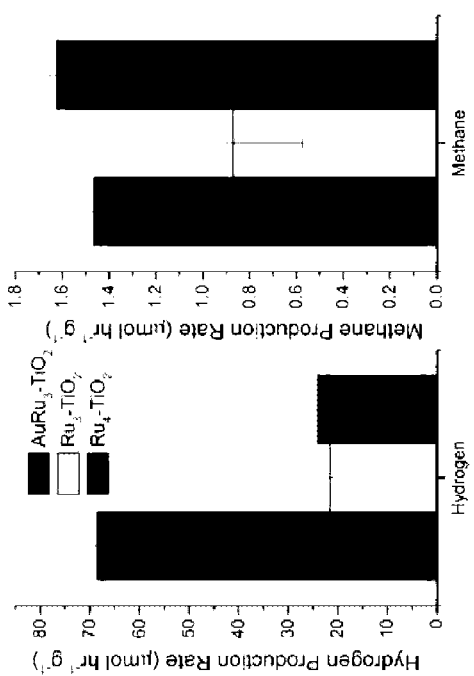
FIG. 18A: Peak production rates of (left) $H_2$ and (right) $CH_4$ by all cluster-deposited titania materials tested here. Standard reaction conditions were used for all tests.

Example 16 a Comparison Between the Catalysts: AuRu/TiO$_2$, Ru$_2$/TiO$_2$ and Ru$_4$/TiO$_2$ Both the Ru$_3$(CO)$_{12}$ precursor of AuRu$_3$ and a H$_4$Ru4 (CO)$_{12}$ cluster deposited upon TiO$_2$ have previously been characterized as catalysts for water-splitting, ethene hydrogenation and Sabatler CO$_2$ reduction. Therefore, these clusters were deposited upon anatase TiO$_2$ and tested for CO$_2$ photo-reduction in the same manner as AuRu$_3$/TiO$_2$. FIGS. 18A and 18B compare the photocatalytic activities of these three cluster species deposited on $TiO_2$ for solar fuel production under UV Irradiation.

Methane and $H_2$ are detected were major products across all three species, with $C_2$-$C_3$ hydrocarbons as minor products. Both $Ru_3$—$TiO_2$ and $Ru_4$—$TiO_2$ also gave off low amounts of CO under UV irradiation; however, the quantities of this varied between scans (potentially due to de-ligation of carbonyl ligands convoluting this signal), and so have been excluded from analysis here. As is clearly evident in FIG. 19, $AuRu_3/TiO_3$ exhibits the highest rate of $H_2$ production out of all three cluster-based systems, with $Ru_3/TiO_2$ and $Ru_3/TiO_2$ giving very similar production rates ~3× lower than this. In terms of methane production, $Ru_3/TiO_2$ again gives the lowest catalytic efficiency, with $Ru_4/TiO_2$ and $AuRu_3/TiO_2$ yielding higher production rates. Within the experimental errors of these measurements, both $AuRu_3/TiO_2$ and $Ru_4/TiO_2$ give comparable methane production rates. Similar trends are observed for most of the minor hydrocarbon products, with large experimental uncertainties in production rates of ethane, propane and propene again preventing further conclusions from being drawn. The exception to this is ethene, for which $Ru_4/TiO_2$ generates appreciably greater amounts than either of the other two photocatalysts. However, hydrocarbon production rates for both $AuRu_3/TiO_2$ and $Ru_4/TiO_2$ are greater than for $Ru_3/TiO_2$. From the above results, it is evident that addition of a single metal atom to the $Ru_3$ cluster—either gold or ruthenium—improves its overall rate of solar fuel production when supported upon anatase titania. However, substitution of gold for a ruthenium atom reduces the $H_2$ generation rate to that of $Ru_3$—$TiO_2$. Therefore, it is likely that the improved $H_2$ production rate of $AuRu_3/TiO_2$ is due to electronic interactions of the gold atom, possibly shifting the cluster's electronic structure to favor $H^-$ reduction or OH oxidation. As the improvement in hydrocarbon production occurs regardless of the added element, this is less likely to be a purely electronic effect, and could more plausibly be due to the increased cluster size allowing for more effective reagent binding.

Figure 19:
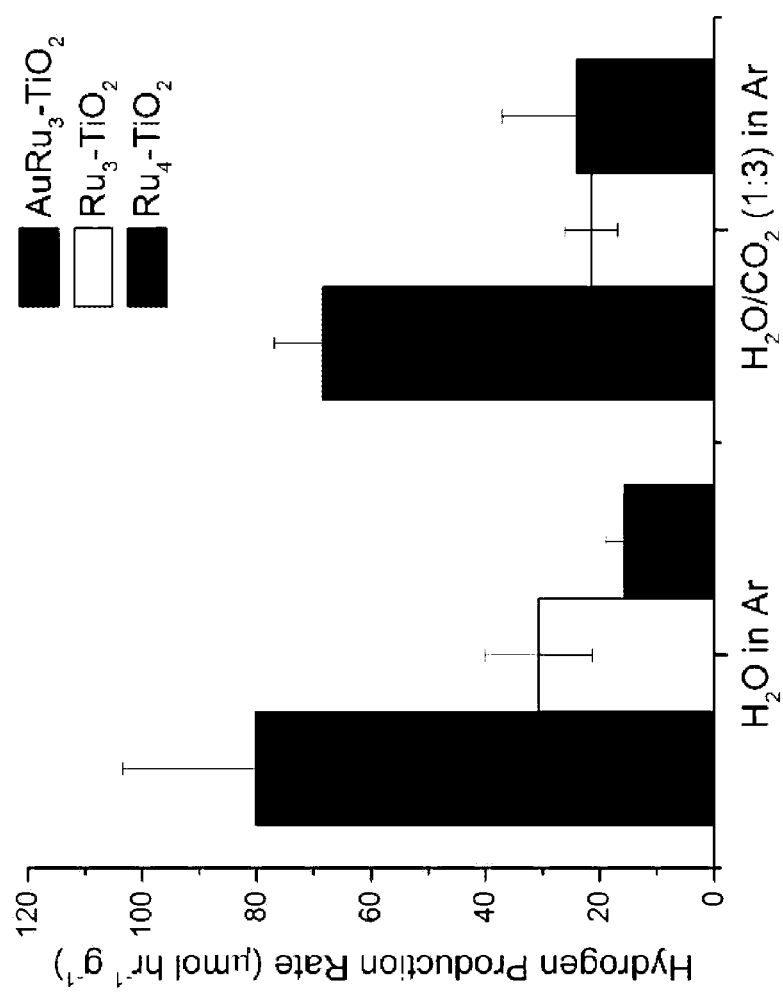
FIG. 19: Peak production rates of $H_2$ by all cluster-deposited titania materials, in atmospheres of $H_2O$/Ar and $H_2O$/$CO_2$/Ar. Standard reaction conditions were used for all tests, with $CO_2$ neglected in the case of $H_2O$/Ar atmospheres.

To assess the potential competitive nature of the water-splitting and $CO_2$ photo-reduction reactions recorded here, these three cluster-based materials were also tested for water-splitting, i.e. in the absence of $CO_2$. FIG. 19 shows the relative $H_2$ production rates from these materials observed under these conditions, alongside the same production rates with $CO_2$ present. Within the experimental uncertainties here, all three clusters exhibit comparable hydrogen production rates both with and without $CO_2$ present in the reaction mixture. This indicates that the presence of $CO_2$ does not hinder the water-splitting reaction for these materials in any way; or conversely, that $CO_2$ does not effectively compete with water for reduction at the photocatalyst surface.

Example 17 Optimising Pre-Treatment Temperature for Au—Ru Catalysts

Heterogeneous catalysts and photocatalysts are generally pre-treated in situ before testing, in order to remove advantageous hydrocarbons and other surface-adsorbed species, or to open up catalyst active sites by removal of ligands. Many different techniques for this can be undertaken for example including ozone treatment, calcination in $O_2$ or $H_2$, and heating under a flow of inert gas. However, the inventors work demonstrates that many of these treatments have damaging effects upon clusters deposited upon $TiO_2$, often causing aggregation to larger nanoparticles. This is undesirable in developing cluster-based catalytic materials, as it removes the size-specific nature of the cluster co-catalysts and complicates the correlation of catalytic activity to particle size. Hence, selection of an appropriate pre-treatment which removes adsorbed contaminants while still retaining intact clusters upon the surface for these materials is paramount.

Figure 20B:
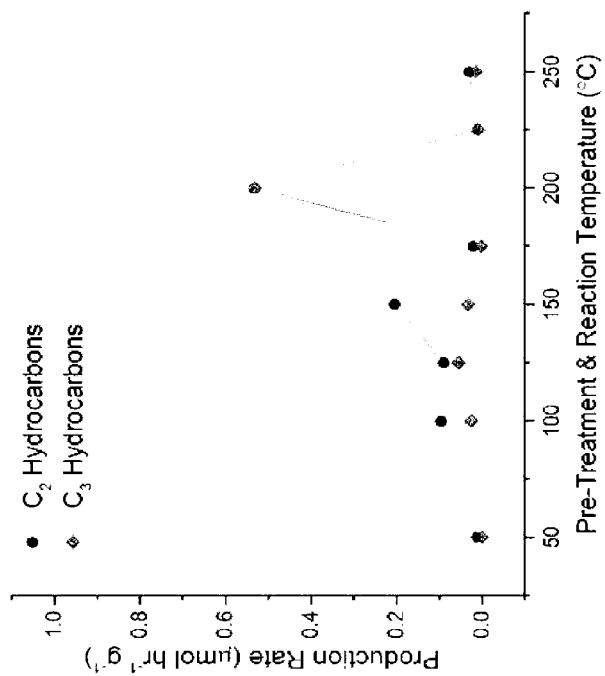
FIG. 20B: Peak production rates of longer-chain hydrocarbon products by $AuRu_3$—$TiO_2$ as a function of combined material pre-treatment and reaction temperature. $P_{CO2}$:$P_{H2O}$=3 for all tests here.
Figure 20A:
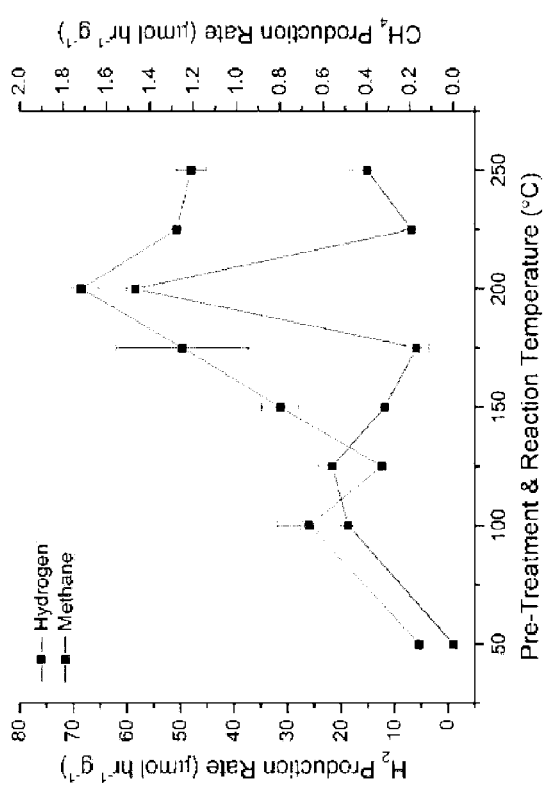
FIG. 20A: Peak production rates of hydrogen and methane by $AuRu_3$—$TiO_2$ as a function of combined material pre-treatment and reaction temperature. $P_{CO2}$:$P_{H2O}$=3 for all tests here.

Heating under vacuum was selected for catalyst pre-treatment, as it was shown to have the least aggregative properties of material treatments studied. All photocatalytic materials discussed above were heated to 200° C. while pumping under vacuum for 20 minutes. However, a range of temperatures from 50-250° C. (the limit of the apparatus) were also tested for $AuRu_3/TiO_2$. FIGS. 20A and 20B show the dependence of photocatalytic activity upon this pre-treatment temperature for major and minor products, respectively. It should be noted that throughout these experiments, the reaction temperature was kept the same as the pre-treatment temperature. This was done to ensure that no samples were tested at higher temperatures than they were pre-treated, such that any observed change in chemical state could be ascribed to the treatment and not the reaction. Using constant, lower reaction temperatures of 50-100° C. could also have achieved this; however as can be seen below, reacting at these temperatures yielded little to no activity. Therefore, it must be acknowledged that the resultant photocatalytic production rates shown in FIGS. 20A & 20B are convoluted also by effects of reaction temperature. The dependence upon reaction temperature will be discussed in Example 18.

Despite this aforementioned convolution of pre-treatment and reaction temperature, an optimal pre-treatment temperature of 200° C. is evident for all products of interest. Production of methane and $C_{2-3}$ hydrocarbons peak at this temperature, with near-baseline production at most other temperatures. Hydrogen production displays a different behaviour, increasing almost linearly from 50-200° C., before then decreasing slightly beyond 200° C. Therefore, a pre-treatment temperature of 200° C. appears to be justified here, as it gives optimal activity towards all products of interest.

Example 18 Optimising Reaction Temperature for Au—Ru Catalysts

Figure 21B:
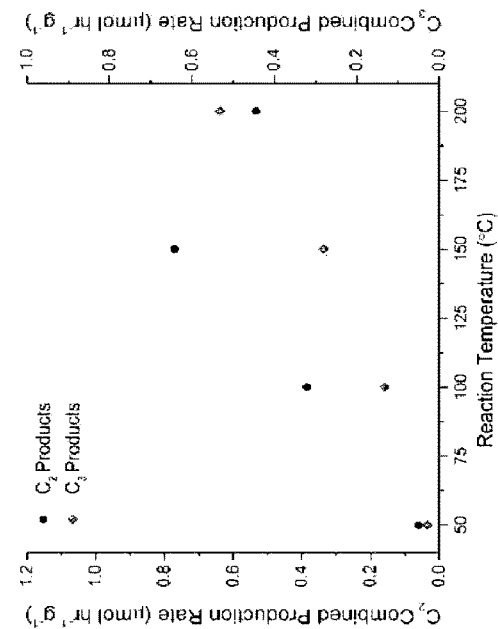
FIG. 21B: Peak production rates of longer-chain hydrocarbon products by $AuRu_3$—$TiO_2$ as a function of reaction temperature. $P_{CO2}$:$P_{H2O}$=3, pre-treatment temperature of 200° C. for all tests here.
Figure 21A:
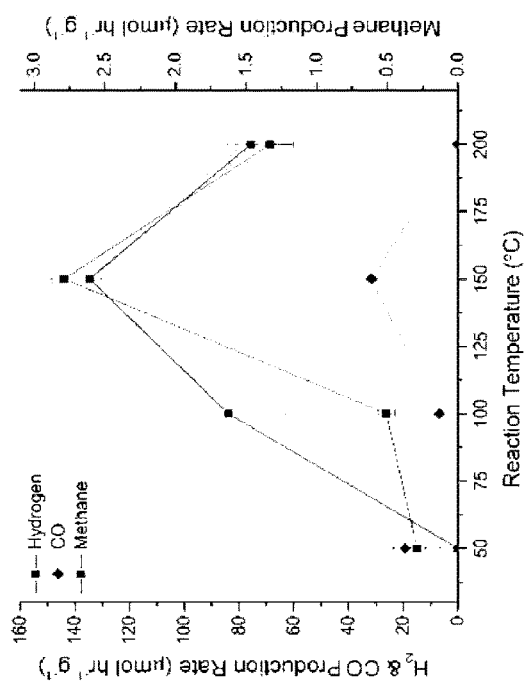
FIG. 21A Peak production rates of hydrogen, methane and CO by $AuRu_3$—$TiO_2$ as a function of reaction temperature. $P_{CO2}$:$P_{H2O}$=3, pre-treatment temperature of 200° C. for all tests here.
Figure 22:
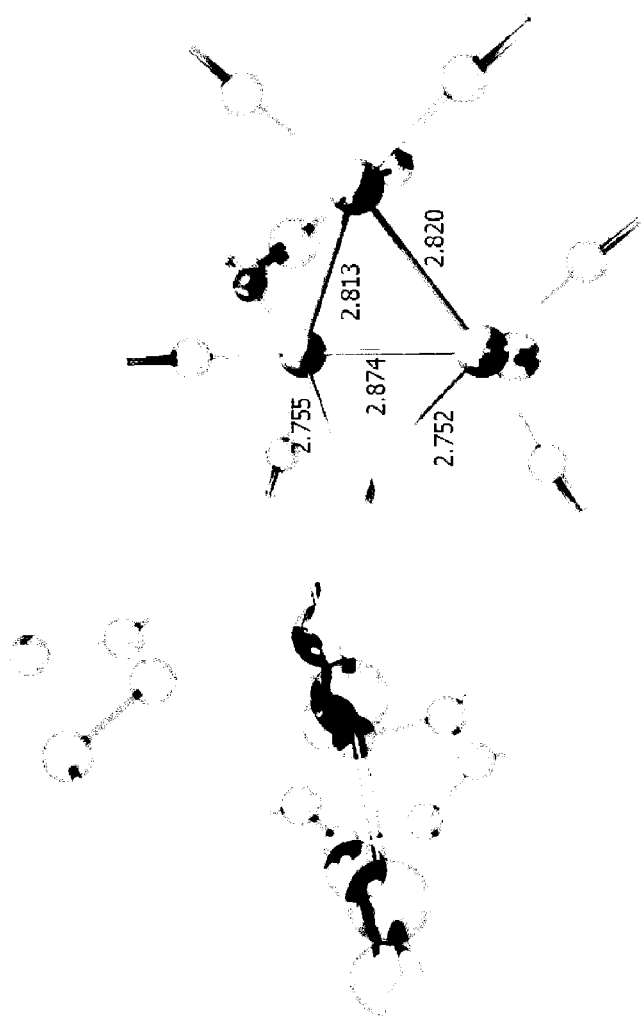
FIG. 22 shows bond distances in $Ru_3(\mu\text{-}AuPPh_3)(\mu\text{-}Cl)(CO)_{10}$.

To de-couple the effects of pre-treatment and reaction temperature, a series of photocatalytic tests on $AuRu_3/TiO_2$ were run over a range of reaction temperatures, while keeping a constant material pre-treatment temperature. 200° C. was chosen as the standard temperature for pre-treatment due to the results from Example 17. FIG. 21A shows the dependence of major product turnovers on reaction temperature, while FIG. 21B shows the same for minor hydrocarbon products detected. Notably, in addition to methane and $H_2$, carbon monoxide was also detected as a major product by GC analysis at some reaction temperatures. As the CO parent ion at m/z=28 overlaps with a fragmentation peak of $CO_2$, RGA analysis could not be used to verify this quantification of CO.

Peak generation rates of most products of interest were observed at a reaction temperature of 150° C. At near-ambient temperatures of 50° C., no appreciable levels of hydrocarbon products are detected, with only $H_2$ and CO observed in low amounts. The first hydrocarbons are detected at a temperature of 100° C., corresponding to a decrease in CO production and a very slight increase in $H_2$ production. Most products follow a very similar trend, increasing in yield from 50-150° C., before decreasing on further raising the temperature to 200° C. The exceptions to this are $C_3$ products such as propane, which have such large experimental uncertainties that no reasonable conclusions can be made; and CO, which shows a decrease from 50-100° C., before peaking at 150° C. like all other products. Several previous works in this field have postulated that CO may be an intermediate species in the reduction of $CO_2$ to hydrocarbons. Hence, the more complex relationship with reaction temperature that CO exhibits here may be due to it being consumed to produce hydrocarbons such as methane or ethane.

A distinctly non-linear relationship with temperature is observed for all products of this photocatalytic reaction. The reaction may be limited by adsorption-desorption effects upon the $TiO_2$ surface, where the rate-limiting step is desorption of products at lower temperatures, and adsorption of reagent molecules at higher temperatures. Reacting at 150° C. may achieve an optimal equilibrium between reagent adsorption and product desorption. At lower temperatures, poor desorption of products or intermediates from water reduction could simultaneously limit the $H_2$ production rate and proton transfer to $CO_2$. As the reaction temperature then increases these reduced states of water would then be mobilized and more readily desorbed, allowing for formation of C—H bonds and giving greater $H_2$ production rates. However, on rising above 150° C. the limiting factor could then become reagent adsorption, with the excess thermal energy in the system causing molecules to desorb from the $TiO_2$ surface before completing photocatalytic transformations and hence decreasing overall production rates.

Conclusions from Examples 15 to 18

When comparing $AuRu_3/TiO_2$ to $Ru_3(CO)_{12}$ or $H_4Ru(CO)_{12}$ clusters deposited upon titania, the bimetallic-deposited species shows the greatest affinity for $H_2$ production from water, while both $M_4$-based clusters show improved hydrocarbon turnover when compared to $Ru_3$—$TiO_2$. Optimal turnover is observed when the photocatalyst was pre-treated under vacuum at 200° C. and reacted at 150° C. and higher partial pressure ratios of $H_2O$ to $CO_2$ improve hydrocarbon production rates. Optimal production of CO and $H_2$ was observed at a reagent ratio of 1:1, and $CO_2$:$H_2O$ ratios in the range of 0.5-4 gave peak hydrocarbon production.

It will be appreciated by persons skilled in the art that numerous variations and/or modifications may be made to the Invention as shown in the specific embodiments without departing from the spirit or scope of the invention as broadly described. The present embodiments are, therefore, to be considered in all respects as Illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for the production of hydrocarbons or substituted hydrocarbons, the method comprising the steps of:
   contacting a catalyst with water and carbon dioxide in the presence of light in order to photocatalyse:
   (i) the splitting of at least some of the water into hydrogen and oxygen; and
   (ii) the reaction between hydrogen and carbon dioxide to produce at least one of a hydrocarbon and a substituted hydrocarbon;
   wherein the catalyst comprises at least gold and ruthenium, in the form of at least one nanocluster supported by a support substrate.

2. The method according to claim 1, wherein support substrate is selected from the group comprising graphene, graphite, carbon black, nanotubes, fullerenes, zeolites, carbon nitrides, metal nitrides and or oxides including zinc oxide or titanium oxide.

3. The method according to claim 1, wherein the gold and ruthenium nanocluster has at least one Au—Ru bond having a distance in the range of from about 2.5 to 3.0 Å.

4. The method according to claim 1, wherein the gold and ruthenium nanocluster comprise an average cluster size less than about 2 nm.

5. The method according to claim 1, wherein the catalyst comprises a first photocatalyst and a second catalyst, the method comprising the steps of:
   a. contacting a first photocatalyst with water in the presence of light in order to photocatalyse the splitting of at least some of the water into hydrogen and oxygen wherein the photocatalyst comprises gold nanoclusters supported by a titanium dioxide substrate; and
   b. contacting a second catalyst with a gas stream comprising carbon dioxide and at least some of the hydrogen produced from step (a) in order to catalyse the reaction between the hydrogen and carbon dioxide to produce at least one of a hydrocarbon and a substituted hydrocarbon;
   wherein said second catalyst comprises ruthenium nanoclusters supported by a titanium dioxide substrate.

6. The method according to claim 5, wherein the titanium dioxide support substrate comprises titanium dioxide nanoparticles.

7. The method according to claim 5, wherein the gold nanoclusters are selected from $(Ph_3PAu)_3OBF_4$, $[(AuPPh_3)_3O]PF_6$, $Au_8(PPh_3)_4Cl$, $Au_6(PPh_3(BF_4)_2$, $Au_6(PPh_3MNO_3)_2$, $Au_6(PPh_3)_6(PF_6)_2$, $Au_8(PPh_3)_8(NO_3)_2$, $Au_8(PPh_3)_7(NO_3)_2$, $Au_9(PPh_3)_8(NO_3)_3$, $Au_{10}(PPh_3)_5(C_6F)_4$, $Au_{11}Cl_3$ $\{(m\text{-}CF_3C_6H_4)_3P\}_7$, $Au_{11}(PPh_3)_7(PF_6)_3$, $[Au_{13}(PMe_2Ph)_{10}Cl_2](PF_6)_3$, $Au_{13}(PPh_3)_4[S(CH_2)_{11}(CH_3)]_4$, $[Au_{13}(PPH_2CH_2PPH_2)_6](NO_3)_4$, $Au_{55}(PH_2PC_6H_4SO_3Na.2H_2O)_{12}Cl_6$, $Au_{55}(PPh_3)_{12}Cl_6$, $Au_{101}(PPh_3)_{21}Cl_5$, where "Ph" is phenyl and "Me" is methyl.

8. The method according to claim 5 wherein the ruthenium nanoclusters comprise either $Ru_3$ or $Ru_4$.

9. The method according to claim 1 wherein the percentage coverage of the support substrate with nanoclusters is at least about 0.1, 0.5, 1, 2, 3, 4, 5 or 10% as a percentage of the total available surface area.

10. The method according to claim 5 wherein the method further includes the step of pre-treating the photocatalyst and/or catalyst prior to use; and
   the pre-treatment includes exposing the photocatalyst and/or catalyst to elevated temperatures under a vacuum, or in the presence of hydrogen or oxygen.

11. The method according to claim 1 wherein the amount of methane produced is at least about 350, 450, 550, 1000, 2000, or 5000 µmol $hr^{-1}$ $g^{-1}$ $cm^{-2}$.

12. The method according to claim 5, wherein substantially all of the hydrogen produced at step (a) is used in step (b).

13. The method according to claim 1 wherein the hydrocarbon is methane.

14. The method according to claim 1 wherein the substituted hydrocarbon is methanol.

15. The method according to claim 1 wherein the amount of hydrogen produced by the method is at least about 15, 50, 80, 100, 150, 200, 250, 350, 450, 550, 1000, 1500, 2000 or 5000 μmol $hr^{-1}$ $g^{-1}$ $cm^{-2}$.

\* \* \* \* \*